(12) United States Patent
Takeda et al.

(10) Patent No.: US 7,575,753 B2
(45) Date of Patent: Aug. 18, 2009

(54) SRSV DETECTION KIT

(75) Inventors: Naokazu Takeda, Tokyo (JP); Katsuro Natori, Tokyo (JP); Tatsuo Miyamura, Tokyo (JP); Kunio Kamata, Gosen (JP); Toshinori Sato, Gosen (JP); Seiya Sato, Gosen (JP)

(73) Assignees: Japan as Represented by Director-General National Institute of Infectious Diseases, Tokyo (JP); Denka Seiken Co., Ltd., Tokyo (JP)

( * ) Notice: Subject to any disclaimer, the term of this patent is extended or adjusted under 35 U.S.C. 154(b) by 224 days.

(21) Appl. No.: 11/402,998

(22) Filed: Apr. 13, 2006

(65) Prior Publication Data

US 2006/0177820 A1    Aug. 10, 2006

Related U.S. Application Data

(62) Division of application No. 09/926,799, filed as application No. PCT/JP00/04095 on Jun. 22, 2000, now Pat. No. 7,067,638.

(30) Foreign Application Priority Data

Jun. 22, 1999    (JP)    ................... 11-175928

(51) Int. Cl.
A61K 39/12    (2006.01)
A61K 39/125    (2006.01)
A61K 39/00    (2006.01)
A61K 39/395    (2006.01)
C12P 7/64    (2006.01)
C12N 15/00    (2006.01)
C12N 5/06    (2006.01)
C12N 5/16    (2006.01)

(52) U.S. Cl. .............. 424/216.1; 424/204.1; 424/186.1; 424/130.1; 424/134.1; 435/134; 435/320.1; 435/333; 435/348; 435/326; 435/331

(58) Field of Classification Search .................. None
See application file for complete search history.

(56) References Cited

U.S. PATENT DOCUMENTS 5,559,014 A    9/1996    Estes et al.
6,156,883 A    12/2000    Estes et al.

FOREIGN PATENT DOCUMENTS

JP    6-506823    8/1994
WO    WO 94/05700    3/1994
WO    WO 97/06823    2/1997

OTHER PUBLICATIONS

K. Natori, et al.: "Chiba virus gene for capsid protein, complete cds, strain: Chiba 407", GenBank Accession No. AB022679, Sep. 1, 1999.

Hiroyuki Saito, et al.: "Application of RT-PCR Designed from the Sequence of the Local SRSV Strain to the Screening in Viral Gastroenteritis Outbreaks.", Microbiology and Immunology, vol. 42, No. 6, pp. 439-446, Jun. 20, 1998.

Jacqueline S. Noel, et al.: "Correlation of Patient Immune Responses with Genetically Characterized Small Round-Structured Viruses Involved in Outbreaks of Nonbacterial Acute Gastroenteritis in the United States, 1990-1995." Journal of Medical Virology, vol. 53, No. 4, pp. 372-383, Dec. 1997.

Lew, et al., Molecular Characterization and Expression of the Capsid Protein of a Norwalk-like Virus Recovered from a Desert Shield Troop with Gastroenteritis. Virology, (1994), vol. 200, No. 1, pp. 319-325.

Database EMBL, "Small Round Structured Virus Genomic RNA, 3' Terminal Sequence Containing ORF 2 and ORF3", Database Accession No. D38547, XP-002305475, Nov. 3, 1994, 3 pages.

Database EMBL, "Capsid Protein", Database Accession No. AB021996, XP-002305476, Jun. 8, 1999, 2 pages.

Antony D. Hale, et al., "Expression and Self-Assembly of Grimsby Virus: Antigenic Distinction from Norwalk and Mexico Viruses", Clinical and Diagnostic Laboratory Immunology, vol. 6, No. 1, XP-002305473, Jan. 1999, pp. 142-145.

Kuniko Kasuga, et al.,: Small round Structured Virus Associated with an Outbreak of Acute Gastroenteritis in Chiba, Japan, Japanese Journal of Medical Science and Biology, vol. 43, No. 4, XP-008038697, 1990, pp. 11-121.

(Continued)

*Primary Examiner*—Bruce Campell
*Assistant Examiner*—Sharon Hurt
(74) *Attorney, Agent, or Firm*—Oblon, Spivak, McClelland, Maier & Neustadt, P.C.

(57) ABSTRACT

This invention relates to an SRSV detection kit comprising all antibodies against SRSV-related virus constituting peptides selected from the following peptide groups (a) to (k), respectively: (a) a peptide having an amino acid sequence represented by SEQ ID NO: 1, and the like, (b) a peptide having an amino acid sequence represented by SEQ ID NO: 2, and the like, (c) a peptide having an amino acid sequence represented by SEQ ID NO: 3, and the like, (d) a peptide having an amino acid sequence represented by SEQ ID NO: 4, and the like, (e) a peptide having an amino acid sequence represented by SEQ ID NO: 5, and the like, (f) a peptide having an amino acid sequence represented by SEQ ID NO: 6, and the like, (g) a peptide having an amino acid sequence represented by SEQ ID NO: 7, and the like, (h) a peptide having an amino acid sequence represented by SEQ ID NO: 8, and the like, (i) a peptide having an amino acid sequence represented by SEQ ID NO: 9, and the like, (j) a peptide having an amino acid sequence represented by SEQ ID NO: 10, and the like, and (k) a peptide having an amino acid sequence represented by SEQ ID NO: 11, and the like.

Use of the kit makes it possible to detect most SRSV-related viruses and further to distinguish their serotypes and genogroups, easily and surely.

9 Claims, 6 Drawing Sheets

OTHER PUBLICATIONS

Jonathan Green, et al., "Capsid Protein diversity Amoung Norwalk-like viruses", Virus Genes, vol. 20, No. 3, XP-002305474, 2000, pp. 227-236.

Database EMBL, Apr. 15, 2000, Green, J.: "Human Calicivirus HU/NLV/Leeds/90 UK RNA for Capsid Protein in (ORF2), Strain HU/NLV/Leeds/90/UK" XP002319156 retrieved from E.B.I. Hinxton U.K., Database accession No. AJ277608 *the whole document*.

Database EMBL, Jan. 7, 1994, Lew, J. et al.: "Calicivirus TV24 Polymerase Gen, Partial Cds, and Capsid Protein Gene, Complete Cds.", XP002319157 retrieved from E.B.I. Hinxton U.K., Database Accession No. U02030 the whole document*.

Database EMBL, Nov. 25, 1994, Lew, J. et al: "Hawaii Calicivirus Polymerase Gene, Partial Cds, and Capsid Protein Gene, Complete Cds." XP002319158 retrieved from E.B.I. Hinxton U.K. Database accession No. U07611 *abstract*.

Kitamoto Noritoshi, et al.: "Cross-Reactivity Amoung Several Recombinant Calicivirus Virus-Like Particles (VLPs) with Monoclonal Antibodies Obtained from Mice Immunized Orally with One Type of VLP." Journal of Clinical Microbiology, Jul. 2002, vol. 40, No. 7, Jul. 2002, pp. 2459-2465, ISSN: 0095-1137.

SEQUENCE LISTING

<160> NUMBER OF SEQ ID NOS: 34

<210> SEQ ID NO 1
<211> LENGTH: 545
<212> TYPE: PRT
<213> ORGANISM: ARTIFICIAL SEQUENCE
<220> FEATURE:
<223> OTHER INFORMATION: SYNETHETIC PEPTIDE

<400> SEQUENCE: 1

```
Met Met Met Ala Ser Lys Asp Ala Pro Thr Asn Met Asp Gly Thr Ser
1               5                   10                  15

Gly Ala Gly Gln Leu Val Pro Glu Ala Asn Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Asn Asn Tyr Val Gln Ala Pro
50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Lys Val Leu
            100                 105                 110

Leu Ala Gly Asn Ala Phe Thr Ala Gly Lys Ile Ile Ile Ser Cys Ile
        115                 120                 125

Pro Pro Gly Phe Ala Ala Gln Asn Ile Ser Ile Ala Gln Ala Thr Met
130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Asn Ala
                165                 170                 175

Pro Thr Met Arg Leu Val Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Ser Phe Leu Phe Leu Val Pro Pro Asn
210                 215                 220

Val Glu Gln Lys Thr Lys Pro Phe Ser Val Pro Asn Leu Pro Leu Asn
225                 230                 235                 240

Thr Leu Ser Asn Ser Arg Val Pro Ser Leu Ile Lys Ser Met Met Val
                245                 250                 255

Ser Arg Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Ser Val Phe His Ala Asn Gly Asn Gly Tyr
290                 295                 300

Asn Leu Thr Glu Leu Asp Gly Ser Pro Tyr His Ala Phe Glu Ser Pro
305                 310                 315                 320

Ala Pro Ile Gly Phe Pro Asp Leu Gly Glu Cys Asp Trp His Met Glu
                325                 330                 335

Ala Ser Pro Thr Thr Gln Phe Asn Thr Gly Asp Val Ile Lys Gln Ile
            340                 345                 350
```

```
Asn Val Lys Gln Glu Ser Ala Phe Ala Pro His Leu Gly Thr Ile Gln
            355                 360                 365

Ala Asp Gly Leu Ser Asp Val Ser Val Asn Thr Asn Met Ile Ala Lys
        370                 375                 380

Leu Gly Trp Val Ser Pro Val Ser Asp Gly His Arg Gly Asp Val Asp
385                 390                 395                 400

Pro Trp Val Ile Pro Arg Tyr Gly Ser Thr Leu Thr Glu Ala Ala Gln
                405                 410                 415

Leu Ala Pro Pro Ile Tyr Pro Pro Gly Phe Gly Glu Ala Ile Val Phe
            420                 425                 430

Phe Met Ser Asp Phe Pro Ile Ala His Gly Thr Asn Gly Leu Ser Val
        435                 440                 445

Pro Cys Thr Ile Pro Gln Glu Phe Val Thr His Phe Val Asn Glu Gln
    450                 455                 460

Ala Pro Thr Arg Gly Glu Ala Ala Leu Leu His Tyr Leu Asp Pro Asp
465                 470                 475                 480

Thr His Arg Asn Leu Gly Glu Phe Lys Leu Tyr Pro Glu Gly Phe Met
                485                 490                 495

Thr Cys Val Pro Asn Ser Ser Gly Thr Gly Pro Gln Thr Leu Pro Ile
            500                 505                 510

Asn Gly Val Phe Val Phe Val Ser Trp Val Ser Arg Phe Tyr Gln Leu
        515                 520                 525

Lys Pro Val Gly Thr Ala Gly Pro Ala Cys Arg Leu Gly Ile Arg Arg
    530                 535                 540

Ser
545

<210> SEQ ID NO 2
<211> LENGTH: 530
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Gly Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160
```

```
Pro Leu Glu Asp Val Arg Asn Val Leu Phe His Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
            195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Gly Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
            275                 280                 285

Lys Ile Arg Gly Thr Ser Asn Gly Thr Val Ile Asn Leu Thr Glu Leu
            290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
            355                 360                 365

Tyr Ile Gly Val Leu Ser Trp Val Ser Pro Ser His Pro Ser Gly
            370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
            405                 410                 415

Val Leu Val Phe Phe Met Ser Lys Ile Pro Gly Pro Gly Ala Tyr Ser
            420                 425                 430

Leu Pro Cys Leu Leu Pro Gln Glu Tyr Ile Ser His Leu Ala Ser Glu
            435                 440                 445

Gln Ala Pro Thr Val Gly Glu Ala Ala Leu Leu His Tyr Val Asp Pro
450                 455                 460

Asp Thr Gly Arg Thr Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
            485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
            515                 520                 525

Arg Arg
    530
```

<210> SEQ ID NO 3
<211> LENGTH: 546
<212> TYPE: PRT
<213> ORGANISM: ARTIFICIAL SEQUENCE
<220> FEATURE:
<223> OTHER INFORMATION: SYNTHETIC PEPTIDE

```
<400> SEQUENCE: 3

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
50                  55                  60

Gln Gly Glu Phe Thr Ile Ser Pro Asn Thr Pro Gly Asp Ile Leu
65              70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
            115                 120                 125

Pro Pro Gly Phe Thr Ser Ser Ser Leu Thr Ile Ala Gln Ala Thr Leu
        130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
        210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
        290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
        370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415
```

```
Ala Pro Pro Val Phe Pro Pro Gly Phe Gly Glu Ala Leu Val Tyr Phe
            420             425             430

Val Ser Ala Phe Pro Gly Pro Asn Asn Arg Ser Ala Pro Asn Asp Val
            435             440             445

Pro Cys Leu Leu Pro Gln Glu Tyr Ile Thr His Phe Val Ser Glu Gln
    450             455             460

Ala Pro Thr Met Gly Asp Ala Ala Leu Leu His Tyr Val Asp Pro Asp
465             470             475             480

Thr Asn Arg Asn Leu Gly Glu Phe Lys Leu Tyr Pro Gly Gly Tyr Leu
            485             490             495

Thr Cys Val Pro Asn Gly Val Gly Ala Gly Pro Gln Gln Leu Pro Leu
            500             505             510

Asn Gly Val Phe Leu Phe Val Ser Trp Val Ser Arg Phe Tyr Gln Leu
            515             520             525

Lys Pro Val Gly Thr Ala Ser Thr Ala Arg Ser Arg Leu Gly Val Arg
            530             535             540

Arg Ile
545

<210> SEQ ID NO 4
<211> LENGTH: 544
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

Met Met Met Ala Ser Lys Asp Ala Thr Pro Ser Ala Asp Gly Ala Thr
1               5                   10                  15

Gly Ala Gly Gln Leu Val Pro Glu Val Asn Thr Ala Asp Pro Ile Pro
            20                  25                  30

Ile Asp Pro Val Ala Gly Ser Ser Thr Ala Leu Ala Thr Ala Gly Gln
        35                  40                  45

Val Asn Leu Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
            115                 120                 125

Pro Pro Gly Phe Gln Ser Arg Thr Leu Ser Ile Ala Gln Ala Thr Leu
        130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
            195                 200                 205

Thr Cys Pro Gly Pro Asp Phe Asn Phe Leu Phe Leu Val Pro Pro Thr
        210                 215                 220
```

-continued

```
Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
            245                 250                 255

Ser Pro Asp Gln Thr Gln Asn Val Gln Phe Gln Asn Gly Arg Cys Thr
        260                 265                 270

Ile Asp Gly Gln Pro Leu Gly Thr Thr Pro Val Ser Val Ser Gln Leu
    275                 280                 285

Cys Lys Phe Arg Gly Arg Ile Thr Ser Gly Gln Arg Val Leu Asn Leu
290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
            325                 330                 335

Lys Ile Pro Asn Ser Ser Thr Gln Asn Asn Pro Ile Val Thr Asn Ser
        340                 345                 350

Val Lys Pro Asn Ser Gln Gln Phe Val Pro His Leu Ser Ser Ile Thr
    355                 360                 365

Leu Asp Glu Asn Val Ser Ser Gly Gly Asp Tyr Ile Gly Thr Ile Gln
370                 375                 380

Trp Thr Ser Pro Pro Ser Asp Ser Gly Gly Ala Asn Thr Asn Phe Trp
385                 390                 395                 400

Lys Ile Pro Asp Tyr Gly Ser Ser Leu Ala Glu Ala Ser Gln Leu Ala
            405                 410                 415

Pro Ala Val Tyr Pro Pro Gly Phe Asn Glu Val Ile Val Tyr Phe Met
        420                 425                 430

Ala Ser Ile Pro Gly Pro Asn Gln Ser Gly Ser Pro Asn Leu Val Pro
    435                 440                 445

Cys Leu Leu Pro Gln Glu Tyr Ile Thr His Phe Ile Ser Glu Gln Ala
450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Tyr Leu Thr
            485                 490                 495

Cys Val Pro Asn Ser Ser Ser Thr Gly Pro Gln Gln Leu Pro Leu Asp
        500                 505                 510

Gly Val Phe Val Phe Ala Ser Trp Val Ser Arg Phe Tyr Gln Leu Lys
    515                 520                 525

Pro Val Gly Thr Ala Gly Pro Ala Arg Gly Arg Leu Gly Val Arg Arg
530                 535                 540
```

<210> SEQ ID NO 5
<211> LENGTH: 539
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45
```

```
Asp Pro Trp Ile Arg Asn Asn Phe Val Gln Ala Pro Gly Gly Glu Phe
 50                  55                  60

Thr Val Ser Pro Arg Asn Ala Pro Gly Glu Ile Leu Trp Ser Ala Pro
 65                  70                  75                  80

Leu Gly Pro Asp Leu Asn Pro Tyr Leu Ser His Leu Ala Arg Met Tyr
                 85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
210                 215                 220

Lys Pro Phe Thr Val Pro Ile Leu Thr Val Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
290                 295                 300

Ser Gln Asn Trp Ser Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Cys Gln Glu Ala
450                 455                 460
```

Ala Pro Ala Gln Ser Asp Val Ala Leu Leu Arg Phe Val Asn Pro Asp
465                 470                 475                 480

Thr Gly Arg Val Leu Phe Glu Cys Lys Leu His Lys Ser Gly Tyr Val
            485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Ala Leu
    530                 535

<210> SEQ ID NO 6
<211> LENGTH: 548
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

Met Lys Met Ala Ser Asn Asp Ala Ala Pro Ser Asn Asp Gly Ala Ala
1               5                   10                  15

Gly Leu Val Pro Glu Ile Asn Asn Glu Ala Met Ala Leu Asp Pro Val
            20                  25                  30

Ala Gly Ala Ala Ile Ala Ala Pro Leu Thr Gly Gln Gln Asn Ile Ile
        35                  40                  45

Asp Pro Trp Ile Met Asn Asn Phe Val Gln Ala Pro Gly Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Ile Asn Pro Tyr Leu Ala His Leu Ala Arg Met Tyr
                85                  90                  95

Asn Gly Tyr Ala Gly Gly Phe Glu Val Gln Val Val Leu Ala Gly Asn
            100                 105                 110

Ala Phe Thr Ala Gly Lys Ile Ile Phe Ala Ala Ile Pro Pro Asn Phe
        115                 120                 125

Pro Ile Asp Asn Leu Ser Ala Ala Gln Ile Thr Met Cys Pro His Val
130                 135                 140

Ile Val Asp Val Arg Gln Leu Glu Pro Val Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Ser Phe Asn Phe Leu Val Pro Pro Thr Val Glu Ser Lys Thr
    210                 215                 220

Lys Pro Phe Thr Leu Pro Ile Leu Thr Ile Ser Glu Met Ser Asn Ser
225                 230                 235                 240

Arg Phe Pro Val Pro Ile Glu Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
        275                 280                 285

```
Val Leu Thr Arg Ser Thr Ser Arg Ala Ser Asp Gln Ala Asp Thr Ala
    290                 295                 300

Thr Pro Arg Leu Phe Asn Tyr Tyr Trp His Val Gln Leu Asp Asn Leu
305                 310                 315                 320

Asn Gly Thr Pro Tyr Asp Pro Ala Glu Asp Ile Pro Gly Pro Leu Gly
                325                 330                 335

Thr Pro Asp Phe Arg Gly Lys Val Phe Gly Val Ala Ser Gln Arg Asn
            340                 345                 350

Leu Asp Ser Thr Thr Arg Ala His Glu Ala Lys Val Asp Thr Thr Ala
        355                 360                 365

Gly Arg Phe Thr Pro Lys Leu Gly Ser Leu Glu Ile Ser Thr Asp Ser
    370                 375                 380

Asp Asp Phe Asp Gln Asn Gln Pro Thr Lys Phe Thr Pro Val Gly Ile
385                 390                 395                 400

Gly Val Asp Asn Glu Ala Glu Phe Gln Gln Trp Ser Leu Pro Asp Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Val Leu Asp Cys Leu Val Pro Gln Glu
    450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Lys Val Leu Phe Glu
                485                 490                 495

Ala Lys Leu His Lys Leu Gly Phe Met Thr Ile Ala Asn Asn Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545

<210> SEQ ID NO 7
<211> LENGTH: 540
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Met Lys Met Ala Ser Asn Asp Ala Thr Pro Ser Asn Asp Gly Ala Ala
1               5                   10                  15

Gly Leu Val Pro Glu Ser Asn Asn Glu Ala Met Ala Leu Glu Pro Val
            20                  25                  30

Val Gly Ala Ser Leu Ala Ala Pro Val Thr Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Val Asn Leu Glu
65                  70                  75                  80

Leu Gly Pro Glu Leu Asn Pro Tyr Leu Ala His Leu Ala Arg Met Tyr
                85                  90                  95
```

-continued

```
Asn Gly Tyr Ala Gly Gly Met Glu Val Gln Val Met Leu Ala Gly Asn
            100                 105                 110

Ala Phe Thr Ala Gly Lys Ile Ile Phe Ala Ala Val Pro Pro Tyr Phe
        115                 120                 125

Pro Val Glu Asn Leu Ser Pro Ser Gln Ile Thr Met Phe Pro His Val
    130                 135                 140

Ile Ile Asp Val Arg Thr Leu Glu Pro Val Leu Leu Pro Met Pro Asp
145                 150                 155                 160

Val Arg Ser Thr Leu Phe His Phe Asn Gln Lys Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Ile Leu Thr Arg Pro Ser Pro
        195                 200                 205

Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240

Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Ser Glu Gln His Met Trp Asn Leu Glu
    290                 295                 300

Ile Thr Asn Leu Asn Gly Thr Gln Phe Asp Pro Thr Asp Val Pro
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350

Ala Val Ala Thr Tyr Ser Asp Lys Tyr Thr Pro Lys Leu Gly Leu
        355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
            420                 425                 430

Phe Phe Arg Ser Tyr Val Pro Leu Lys Gly Gly Phe Gly Asn Pro Ala
        435                 440                 445

Ile Asp Cys Ser Val Pro Gln Glu Trp Val Gln His Phe Tyr Gln Glu
    450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Pro Ala Asn
            500                 505                 510
```

-continued

Gly Tyr Phe Lys Phe Asp Ser Trp Val Asn Gln Phe Tyr Ser Leu Ala
            515                 520                 525

Pro Met Gly Thr Gly Asn Gly Arg Arg Arg Val Gln
530                 535                 540

<210> SEQ ID NO 8
<211> LENGTH: 535
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Met Lys Met Ala Ser Asn Asp Ala Ala Pro Ser Asn Asp Gly Ala Ala
1               5                   10                  15

Gly Leu Val Pro Glu Ala Asn Asn Glu Thr Met Ala Leu Glu Pro Val
            20                  25                  30

Ala Gly Ala Ser Ile Ala Ala Pro Leu Thr Gly Gln Asn Asn Ile Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Leu Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asn Gly Thr Pro Phe Asp Pro Thr Gly Asp Val Pro
305                 310                 315                 320

Ala Pro Leu Gly Thr Pro Asp Phe Ser Gly Lys Leu Phe Gly Val Leu
                325                 330                 335

-continued

```
Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
            355                 360                 365

Gly Thr Trp Glu Glu Asp Val His Ile Asn Gln Pro Thr Lys Phe
370                 375                 380

Thr Pro Val Gly Leu Phe Glu Asn Glu Gly Phe Asn Gln Trp Thr Leu
385                 390                 395                 400

Pro Asn Tyr Ser Gly Ala Leu Thr Leu Asn Met Gly Leu Ala Pro Pro
                405                 410                 415

Val Ala Pro Thr Phe Pro Gly Glu Gln Ile Leu Phe Phe Arg Ser His
            420                 425                 430

Ile Pro Leu Lys Gly Gly Val Ala Asp Pro Val Ile Asp Cys Leu Leu
            435                 440                 445

Pro Gln Glu Trp Ile Gln His Leu Tyr Gln Glu Ser Ala Pro Ser Gln
    450                 455                 460

Ser Asp Val Ala Leu Ile Arg Phe Thr Asn Pro Asp Thr Gly Arg Val
465                 470                 475                 480

Leu Phe Glu Ala Lys Leu His Arg Ser Gly Tyr Ile Thr Val Ala Asn
                485                 490                 495

Thr Gly Ser Arg Pro Ile Val Val Pro Ala Asn Gly Tyr Phe Arg Phe
            500                 505                 510

Asp Thr Trp Val Asn Gln Phe Tyr Ser Leu Ala Pro Met Gly Thr Gly
            515                 520                 525

Asn Gly Arg Arg Arg Val Gln
            530                 535
```

<210> SEQ ID NO 9
<211> LENGTH: 542
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

```
Met Lys Met Ala Ser Asn Asp Ala Ala Pro Ser Asn Asp Gly Ala Ala
1               5                   10                  15

Ser Leu Val Pro Glu Gly Ile Asn Glu Thr Met Pro Leu Glu Pro Val
            20                  25                  30

Ala Gly Ala Ser Ile Ala Ala Pro Val Ala Gly Gln Thr Asn Ile Ile
            35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Ile Pro Pro Asn Phe
            115                 120                 125

Leu Val Asp Met Ile Ser Pro Ala Gln Ile Thr Met Leu Pro His Leu
    130                 135                 140

Ile Val Asp Val Arg Thr Leu Glu Pro Ile Met Thr Pro Leu Pro Asp
145                 150                 155                 160
```

Val Arg Asn Val Phe Tyr His Phe Asn Asn Gln Pro Gln Pro Arg Met
            165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
            195                 200                 205

Asp Phe Glu Phe Ile Tyr Leu Val Pro Pro Ser Val Glu Ser Lys Thr
210                 215                 220

Lys Pro Phe Thr Leu Pro Ile Leu Thr Ile Ser Glu Leu Thr Asn Ser
225                 230                 235                 240

Arg Phe Pro Ile Pro Ile Glu Gln Leu Tyr Thr Ala Pro Asn Glu Thr
            245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Phe Leu Gln Gly
            275                 280                 285

Arg Thr Val Ala Asp Asn Gly Asp Asn Trp Asp Gln Asn Leu Leu Gln
            290                 295                 300

Leu Thr Tyr Pro Asn Gly Ala Ser Tyr Asp Pro Thr Asp Glu Val Pro
305                 310                 315                 320

Ala Pro Leu Gly Thr Gln Asp Phe Ser Gly Met Leu Tyr Gly Val Leu
            325                 330                 335

Thr Gln Asp Asn Val Asn Val Ser Thr Gly Glu Ala Lys Asn Ala Lys
            340                 345                 350

Gly Ile Tyr Ile Ser Thr Thr Ser Gly Lys Phe Thr Pro Lys Ile Gly
            355                 360                 365

Ser Ile Gly Leu His Ser Ile Thr Glu His Val His Pro Asn Gln Gln
370                 375                 380

Ser Arg Phe Thr Pro Val Gly Val Ala Val Asp Glu Asn Thr Pro Phe
385                 390                 395                 400

Gln Gln Trp Val Leu Pro His Tyr Ala Gly Ser Leu Ala Leu Asn Thr
            405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
            435                 440                 445

Ala Phe Ile Asp Cys Leu Leu Pro Gln Glu Trp Val Asn His Phe Tyr
450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
            485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
            515                 520                 525

Leu Ala Pro Met Gly Thr Gly Asn Gly Arg Arg Arg Ile Gln
530                 535                 540

<210> SEQ ID NO 10
<211> LENGTH: 550
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 10

```
Met Lys Met Ala Ser Asn Asp Ala Ala Pro Ser Asn Asp Gly Ala Ala
1               5                   10                  15

Asn Leu Val Pro Glu Ala Asn Asp Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Ser Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Pro Arg Met
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Thr Leu Pro Ile Leu Thr Leu Gly Glu Leu Ser Asn Ser Arg
225                 230                 235                 240

Phe Pro Ala Ala Ile Asp Met Leu Tyr Thr Asp Pro Asn Glu Ser Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Ser Gln Thr Ala Arg Ala Ala Asp Ser Thr Asp Ser Pro Gln
    290                 295                 300

Arg Ala Arg Asn His Pro Leu His Val Gln Val Lys Asn Leu Asp Gly
305                 310                 315                 320

Thr Gln Tyr Asp Pro Thr Asp Ile Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Glu Gln Gly His Tyr Ala Thr Arg Ala His Glu Ala His
        355                 360                 365

Ile Asp Thr Thr Asp Pro Lys Tyr Ala Pro Lys Leu Gly Thr Ile Leu
    370                 375                 380

Ile Lys Ser Gly Ser Asp Asp Phe Asn Thr Asn Gln Pro Ile Arg Phe
385                 390                 395                 400

Thr Pro Val Gly Met Gly Asp Asn Asn Trp Arg Gln Trp Glu Leu Pro
                405                 410                 415
```

```
Asp Tyr Ser Gly Arg Leu Thr Leu Asn Met Asn Leu Ala Pro Ala Val
            420                 425                 430

Ser Pro Ser Phe Pro Gly Glu Arg Ile Leu Phe Phe Arg Ser Ile Val
            435                 440                 445

Pro Ser Ala Gly Gly Tyr Gly Ser Gly Tyr Ile Asp Cys Leu Ile Pro
            450                 455                 460

Gln Glu Trp Val Gln His Phe Tyr Gln Glu Ala Ala Pro Ser Gln Ser
465                 470                 475                 480

Ala Val Ala Leu Val Arg Tyr Val Asn Pro Asp Thr Gly Arg Asn Ile
                485                 490                 495

Phe Glu Ala Lys Leu His Arg Glu Gly Phe Leu Thr Val Ala Asn Cys
                500                 505                 510

Gly Asn Asn Pro Ile Val Val Pro Pro Asn Gly Tyr Phe Arg Phe Glu
            515                 520                 525

Ala Trp Gly Asn Gln Phe Tyr Thr Leu Ala Pro Met Gly Ser Gly Gln
            530                 535                 540

Gly Arg Arg Arg Ala Gln
545                 550

<210> SEQ ID NO 11
<211> LENGTH: 541
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

Met Lys Met Ala Ser Asn Asp Ala Ala Pro Ser Ser Asp Gly Ala Ala
1               5                   10                  15

Gly Leu Val Pro Glu Ile Asn Asn Glu Val Met Pro Leu Glu Pro Val
            20                  25                  30

Ala Gly Ala Ser Leu Ala Thr Pro Val Val Gly Gln Gln Asn Ile Ile
            35                  40                  45

Asp Pro Trp Ile Arg Asn Asn Phe Val Gln Ala Pro Ala Gly Glu Phe
        50                  55                  60

Thr Val Ser Pro Arg Asn Ser Pro Gly Glu Ile Leu Leu Asp Leu Glu
65                  70                  75                  80

Leu Gly Pro Asp Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Ile Phe Ala Ala Ile Pro Pro Gly Phe
            115                 120                 125

Pro Tyr Glu Asn Leu Ser Pro Ser Gln Ile Thr Met Cys Pro His Val
        130                 135                 140

Ile Ile Asp Val Arg Gln Leu Glu Pro Phe Leu Leu Pro Met Pro Asp
145                 150                 155                 160

Ile Trp Asn Asn Phe Phe His Tyr Asn Gln Gly Asn Asp Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Lys Pro Ser Pro
        195                 200                 205

Asp Phe Glu Phe Thr Phe Leu Val Pro Pro Thr Val Glu Ser Lys Thr
210                 215                 220
```

```
Lys Gln Phe Ala Leu Pro Ile Leu Lys Ile Ser Glu Met Thr Asn Ser
225                 230                 235                 240

Arg Phe Pro Val Pro Val Asp Val Met Tyr Thr Ala Arg Asn Glu Asn
            245                 250                 255

Gln Val Val Gln Pro Gln Asn Gly Arg Val Thr Leu Asp Gly Glu Leu
        260                 265                 270

Leu Gly Thr Thr Pro Leu Leu Ala Val Asn Ile Cys Lys Phe Lys Gly
    275                 280                 285

Glu Val Ile Ala Lys Asn Gly Asp Val Arg Ser Tyr Arg Met Asp Met
290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
            325                 330                 335

Ala Ser Gln Arg Asn Lys Asn Glu Gln Asn Pro Ala Thr Arg Ala His
        340                 345                 350

Glu Ala Ile Ile Asn Thr Gly Gly Asp His Leu Cys Pro Gln Ile Ser
    355                 360                 365

Ser Ser Glu Ile Tyr Leu Thr Ser Pro Asn Ile Leu Arg Cys Thr Asn
370                 375                 380

Pro Gln Pro Leu Pro Gln Ser Gly Leu Arg Gly Thr Ile Leu Ile Arg
385                 390                 395                 400

Ser Asp Asn Gly His Cys His Asp Met Val Gly Thr Ser Pro Thr Thr
            405                 410                 415

Pro Thr Trp Pro Gln Gln Trp Arg Arg Cys Ser Arg Gly Ser Asn Cys
        420                 425                 430

Cys Ser Ser Gly His Arg Tyr Pro Val Pro Val Val Met Asn Arg Val
    435                 440                 445

Thr Trp Ile Val Leu Ser His Lys Ser Gly Phe Ser Thr Ser Thr Arg
450                 455                 460

Lys Leu Pro Gln Leu Asn Leu Arg Trp Pro Leu Ile Arg Phe Ile Asn
465                 470                 475                 480

Pro Asp Thr Gly Arg Val Leu Phe Glu Ala Arg Leu His Lys Gln Gly
            485                 490                 495

Phe Ile Thr Val Ala His Thr Gly Asp Asn Pro Ile Val Met Pro Pro
        500                 505                 510

Asn Gly Tyr Phe Arg Phe Glu Ala Trp Val Asn Gln Phe Tyr Ser Leu
    515                 520                 525

Ala Pro Val Gly Thr Gly Lys Gly Arg Arg Arg Val Gln
530                 535                 540

<210> SEQ ID NO 12
<211> LENGTH: 1638
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
atgatgatgg cgtctaagga cgccccaaca acatggatg gcaccagtgg tgccggccag      60
ctggtaccag aggcaaatac agctgagcct atatcaatgg agcctgtggc tggggcagca     120
acagctgccg caaccgctgg ccaagttaat atgattgacc cctggataat gaataattat     180
gtgcaagccc ctcaaggtga atttaccata tcgcctaata acaccaggt gatattttg       240 tttgatctac aattaggccc tcatctcaat cctttcttat cccatttggc ccaaatgtat     300
```

| | |
|---|---:|
| aacggttggg ttggcaatat gaaagtgaag gtcctattgg ctggtaatgc cttcacggct | 360 |
| ggtaaaataa tcattagttg catacccct ggctttgctg cgcaaaacat ttctatcgct | 420 |
| caggccacaa tgttccccca cgttatagct gatgttaggg ttttggaacc tattgaggtg | 480 |
| ccattggaag atgtgaggaa tgtgctgttc ataacaatg acaacgcacc aaccatgagg | 540 |
| ttggtgtgca tgctctacac ccccttgcga gccagtggta gctcatctgg aactgaccct | 600 |
| tttgtgattg ctgggcgtgt tctgacatgc ccaagccctg actttagctt cttattcttg | 660 |
| gttcccccca atgtagagca aaagactaaa ccttttagtg tcccaaatct tccactgaat | 720 |
| acccttcaa attcaagagt cccttctcta attaaatcaa tgatggtatc cagagaccat | 780 |
| gggcagatgg ttcagtttca aaacggtagg gtcaccctgg atgggcaact gcaaggcacc | 840 |
| acgcccacat cagctagcca gctgtgcaaa atcagaggca gtgtcttcca tgctaatggt | 900 |
| gggaatggat ataacctaac tgaattggat gggagcccat accatgcttt tgagagccct | 960 |
| gcgccaatag gtttcctga tctaggtgaa tgtgattggc acatggaggc ctcccctacc | 1020 |
| acccaattca atactggtga tgttataaaa caaattaatg tcaaacaaga atcagcattt | 1080 |
| gctccccacc ttggtaccat acaagcagat ggcctgagtg atgtgagtgt caacactaac | 1140 |
| atgatagcca aattgggatg ggtgtcaccc gtcagtgatg gacatagagg agatgtcgat | 1200 |
| ccgtgggtca ttccacgata tgggtcgact ttgaccgagg ccgcccaatt agccccccca | 1260 |
| atatatcccc caggttttgg tgaggccatt gtgttttca tgtcagattt tcctatagcc | 1320 |
| catggtacca atggcttgag tgtgccttgc accataccc aagaatttgt cacccatttt | 1380 |
| gtcaatgaac aggcccctac tagaggggaa gcagccctac tgcattattt agaccctgat | 1440 |
| acccatagaa atcttggtga gtttaaatta taccctgagg ggttcatgac gtgtgtgcct | 1500 |
| aattccagtg gcactggtcc acaaaccctc ccaatcaatg gtgttttgt ttttgtgtcc | 1560 |
| tgggtttcca gattctatca gttaaagcct gtgggaacag ccggcccggc ttgtaggctt | 1620 |
| ggcatcagaa gatcataa | 1638 |

<210> SEQ ID NO 13
<211> LENGTH: 1593
<212> TYPE: DNA
<213> ORGANISM: ARTIFICIAL SEQUENCE
<220> FEATURE:
<223> OTHER INFORMATION: SYNTHETIC DNA

<400> SEQUENCE: 13

| | |
|---|---:|
| atgatgatgg cgtctaagga cgctacgtca agcgtggatg gcgccagtgg cgctggtcag | 60 |
| ttggtaccgg aggttaatgc ttctgaccct cttgcaatgg atcctgtggc gggttcttca | 120 |
| acagcagttg caactgctgg gcaagttaac cctattgacc cttggataat caataacttt | 180 |
| gtgcaggctc cccaaggtga atttactatt tctccaaata taccccggg tggtgttttg | 240 |
| tttgatttga gtctaggccc tcatcttaat cccttcttgt tacatttgtc acaaatgtat | 300 |
| aatggctggg ttggcaacat gagagttagg attatgctgg ctggtaatgc atttactgca | 360 |
| ggcaaaatta tagtttcttg catacctcct ggctttggct cccataatct tactatagca | 420 |
| caagcaactc tcttcccgca tgtgattgct gatgttagga ctttagaccc aattgaagta | 480 |
| ccccttggaag atgtaaggaa tgtctctttt cataataatg atagaaatca acaaccatg | 540 |
| cgccttgtgt gtatgctttta taccccctc cgcactggtg gcggtacagg tgattctttt | 600 |
| gtggttgcag ggcgagtcat gacttgtcct agccccgatt tcaatttctt gttcttggtt | 660 |
| cctcccacag tggaacagaa gactaggcct ttcaccctcc caaatttacc gctgagttct | 720 |

```
ttgtcaaatt cacgtgctcc tcttccaatt agtggcatgg gtatttctcc agacaatgtt      780
cagagtgtgc agtttcaaaa tggccgatgt accttagacg ggcgtcttgt tggtaccacc      840
ccagtttccc tctcccacgt tgctaagata aggggcactt ctaatggtac tgtgatcaat      900
ctcaccgaat tggatggcac ccccttccac ccttttgaag gccctgcccc tattggtttt      960
ccagatcttg gtggctgtga ttggcatatt aatatgacac aatttgggca ttccagtcag     1020
actcaatatg atgtagatac caccccccgac accttcgtcc ctcacttagg ttcaatccag     1080
gcgaatggca ttggtagtgg caactatatt ggtgttctta gctgggtctc cccccccatca     1140 catccatctg gctctcaagt tgatctctgg aagatcccca actatgggtc tagcatcaca     1200
gaggcaaccc atctagctcc ctctgtctat cctcctggct ttggagaggt gttagtctt      1260 ttcatgtcaa agatacctgg tcctggtgct atagtctgc cctgtttact gccacaagaa      1320
tatatctcac acctcgcaag tgaacaagcc cccactgttg gtgaggccgc cttgctccac     1380
tatgttgacc ctgacacggg ccggactctt ggggagttta aggcttaccc tgatggtttc     1440
ctaacctgtg tccctaacgg ggccagctcg ggcccacaac aactaccaat caatggagtc     1500
tttgtctttg tttcatgggt gtccagattt tatcagttaa agcctgtggg aactgccagt     1560
tcggcaagag gtaggcttgg tttgcgccga taa                                  1593

<210> SEQ ID NO 14
<211> LENGTH: 1641
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
atgatgatgg cgtctaagga cgcccctcaa agcgctgatg gcgcaagcgg cgcaggtcaa       60
ctggtgccgg aggttaatac agctgacccc ttacccatgg aaccgtggc tgggccaaca      120 acagccgtag ccactgctgg gcaagttaat atgattgatc cctggattgt aataattttt      180
gtccagtcac acaaggtga gtttacaatt tcccctaata ataccccgg tgatattttg       240 tttgatttac aattaggtcc acatctaaac cctttcttgt cacatctgtc ccaaatgtat      300
aatggctggg ttggaaacat gagagttagg attctccttg ctgggaatgc attctcagct      360
ggaaagatta tagtttgttg tgtcccccct ggctttacat cttcctctct caccatagct      420
caggctacat tgtttcccca tgtgattgct gatgtgagaa cccttgaacc aatagaaatg      480
cccctcgagg atgtacgcaa tgtcctctat cacaccaatg ataatcaacc aacaatgcgg      540
ttggtgtgta tgctgtacac gccgctccgc actggtgggg gtctggtaa ttctgattct      600 tttgtggttg ctggcagggt gctcacggcc ctagtagcac acttcagttt cttgttcctt      660
gtcccgccta ccatagaaca gaagactcgg gcttttactg tgcctaatat ccccttgcaa      720
accttgtcca attctaggtt tccttccctc atccagggga tgattctgtc tcctgacgca      780
tctcaagtgg tccaattcca aaatggacgt tgcctcatag atggtcaact cctaggcact      840
acacccgcta catcaggaca gctgttcaga gtaagaggaa agataaatca gggagcccgt      900
acgctcaacc tcacagaggt ggatggcaaa ccattcatgg catttgattc ccctgcacct      960 gtgggggttcc ccgattttgg aaaatgtgat tggcacatga gaatcagcaa acccccaaat    1020
aacacaagct caggtgaccc catgcgcagt gtcagcgtgc aaaaccaatgt gcagggtttt     1080 gtgccacacc taggaagtat acagtttgat gaagtgttca accaccccac aggtgactac     1140
attggcacca ttgaatggat tcccagcca tctacacccc ctggaacaga tattaatctg      1200
```

```
tgggagattc  cgattatgg   atcatccctt  tcccaagcag  ctaatctggc  cccccagta    1260 ttccccctg   gatttggtga  ggctcttgtg  tactttgttt  ctgcttttcc  aggcccaac    1320 aaccgctcag  ccccgaatga  tgtaccttgt  cttctccctc  aagagtacat  aacccacttt   1380
gtcagtgaac  aagcccaac   gatgggtgac  gcagctttgc  tgcattatgt  cgaccctgat   1440
accaacagaa  accttgggga  gttcaagcta  taccctggag  gttacctcac  ctgtgtacca   1500 aacgggtgg   gtgccgggcc  tcaacagctt  cctcttaatg  gtgtctttct  ctttgtctct   1560
tgggtgtctc  gtttttatca  gctcaagcct  gtgggaacag  ccagtacggc  aagaagtagg   1620
cttggagtgc  gccgtatata  a                                                1641

<210> SEQ ID NO 15
<211> LENGTH: 1635
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
atgatgatgg   cgtctaagga  cgctacacca  agcgcagatg  gcgccactgg  cgccggccag    60
ctggtaccgg   aggttaatac  agctgacccc  atacctattg  accctgtggc  tggctcctct   120
acagcccttg   ccacagcagg  ccaggttaat  ttgattgatc  cctggataat  caataatttt   180
gtgcaagccc   cccagggcga  gttcacaata  tccccaaata  taccccggg   tgatgtgctt   240 tttgatttgc   aattaggacc  ccatttaaat  cctttccttt  cccaccttt   tcagatgtat   300 aatggttggg   tgggcaacat  gcgagtgcgt  gttgtcttgg  ctggtaatgc  tttcacggct   360
gggaaggtta   taatttgttg  tgtcccccct  ggtttccaat  ctcgcaccct  ttctatagcc   420
caggctactt   tatttcccca  tgtaattgct  gatgttagga  cccttgaccc  tgtagaagtg   480
ccccttgaag   atgttaggaa  tgtgttgtat  cataataatg  acaccaacc   caccatgcgc   540 ctcctttgca   tgttgtacac  tcctctccgc  accgggggag  cgtctggtgg  gactgattct   600
tttgtggtgg   ctgggcgtgt  actcacttgt  ccgggccctg  actttaactt  cttattccta   660
gtccctccca   cagtcgagca  aaagaccgc   ccttttactg  tgcctaatat  ccctttgaag   720
tacctgtcta   attccaggat  cccaaatcct  attgaaggta  tgtcattgtc  acctgaccag   780
acccaaaatg   ttcaattcca  gaatggtagg  tgtacaattg  acggtcaacc  ccttgggacc   840
acacctgtct   cagttagtca  gttatgtaag  tttaggggta  ggattacatc  tggacagaga   900
gtgctcaact   tgacagagtt  ggatggttca  ccttttatgg  cctttgccgc  cccgcccct   960 gcgggctttc   cagatcttgg  gtcctgtgat  tggcatattg  aaatgagtaa  atcccaaat   1020 tccagcaccc   agaacaaccc  aatagtgacc  aattctgtca  aacccaatag  tcaacagttt   1080
gtcccacact   tgtcaagtat  cacccttgat  gaaaatgttt  ccagtggagg  tgactatatt   1140
ggcactatac   aatggaccctc acctccttct  gattctggcg  gggccaatac  aaattttgg    1200 aaatccctg    actatgggtc  cagcctagca  gaagcttcac  aactggcccc  cgctgtctat   1260
ccacctggtt   tcaatgaggt  gattgtgtat  tttatggcat  ctatacctgg  tcccaatcag   1320
tctgggtctc   ctaatttagt  gccatgcctg  ctccccagg   aatatataac  acactttatt   1380
agtgagcagg   ccccatcca   gggtgaggct  gccttactcc  actatgtaga  cccagacacc   1440
aatcgcaatt   tgggtgagtt  caatttatat  cctggtggtt  attaacctg   tgttcctaat   1500 agttctagta   ctggacctca  acaacttcct  cttgatggtg  tatttgtctt  tgcttcttgg   1560
```

-continued

| gtttctagat tttatcaatt aaagcctgtg ggaacagccg gaccggctag aggtaggctt | 1620 |
| ggtgtccgta gataa | 1635 |

<210> SEQ ID NO 16
<211> LENGTH: 1620
<212> TYPE: DNA
<213> ORGANISM: ARTIFICIAL SEQUENCE
<220> FEATURE:
<223> OTHER INFORMATION: SYNTHETIC DNA

<400> SEQUENCE: 16

| atgaagatgg cgtcgaatga cgccaaccca tctgatgggt ccacagccaa cctcgtccca | 60 |
| gaggtcaaca atgaggttat ggctttggag cccgttgttg gtgccgctat gcggcacct | 120 |
| gtagcgggcc aacaaaatgt aattgacccc tggattagaa ataattttgt acaagcccct | 180 |
| ggtggagagt ttacagtatc ccctagaaac gctccgggtg agatattatg gagcgcgccc | 240 |
| ttgggccctg atttgaaccc ctacctttct catttggcca gaatgtacaa tggttatgca | 300 |
| ggtggttttg aagtgcaggt aatcctcgcg ggaacgcgt tcaccgccgg gaaaatcata | 360 |
| tttgcagcag tcccaccaaa ttttccaact gaaggcttga gccccagcca ggttactatg | 420 |
| ttcccccata ataagtaga tgttaggcaa ttggaacctg tattgatccc cttacctgat | 480 |
| gttaggaata acttctatca ttacaatcaa tcaaatgatt ctaccattaa attgatagca | 540 |
| atgctgtata caccacttag ggctaataat gctggggatg atgtcttcac agtctcttgt | 600 |
| cgagtcctca cgaggccatc cccgattttt gatttcatat tcttggtgcc acccacagtt | 660 |
| gaatcaagaa ctaaaccatt caccgtccca atcttaactg ttgaggaaat gtctaactca | 720 |
| agattcccca ttcctttgga aaagttgtac acgggtccca gcagtgcttt tgttgtccaa | 780 |
| ccacaaaatg gcaggtgcac gactgatggc gtgctcttag cactaccca gctgtctgct | 840 |
| gtcaacatct gcaccttcag agggggatgtc acccacattg caggcagtca tgactataca | 900 |
| atgaatttgg cttctcaaaa ttggagcaat tatgacccaa cagaagaaat cccagcccct | 960 |
| ctgggaactc cagatttcgt gggaaagatc caaggcatgc tcacccaaac cacaagagag | 1020 |
| gatggctcga cccgcgccca caagctaca gtgagcactg ggagtgtcca cttcactcca | 1080 |
| aagctgggca gtgttcaata caccactgac acaaacaatg atttttcaaac tggccaaaac | 1140 |
| acgaaattca ccccagtcgg cgtcatccag gacggtaata atcatcaaaa tgaaccccaa | 1200 |
| caatgggtgc tcccaaatta ctcaggtaga actggtcata atgtgcacct agctcctgcc | 1260 |
| gttgcccca ctttcccggg tgagcaactt cttttcttta ggtccactat gcccggatgt | 1320 |
| agcgggtatc ctaacatgaa tctggattgc ctactccccc aggaatgggt gcaacacttc | 1380 |
| tgccaagaag cagctccagc acaatctgat gtggctctgc tgagatttgt gaatccagac | 1440 |
| acaggtaggg ttttgtttga gtgcaagctc cataaatcag gctatgtcac agtggctcac | 1500 |
| actggcccgc atgatttggt tatccccccc aatggttact ttagatttga ctcctgggtc | 1560 |
| aaccagttct acacacttgc ccccatggga aatggagcgg ggcgcaggcg tgcattataa | 1620 |

<210> SEQ ID NO 17
<211> LENGTH: 1647
<212> TYPE: DNA
<213> ORGANISM: ARTIFICIAL SEQUENCE
<220> FEATURE:
<223> OTHER INFORMATION: SYNTHETIC DNA

```
<400> SEQUENCE: 17
atgaagatgg cgtcgaatga cgctgctcca tctaatgatg gtgccgccgg cctcgtccca      60
gagatcaaca atgaggcaat ggcgctagac ccagtggcgg gtgcagcgat agcagcgccc     120
ctcactggtc agcaaaacat aattgatccc tggattatga ataattttgt gcaagcacct     180
ggtggtgagt ttacagtgtc ccctaggaat tcccctggtg aagtgcttct taatttggaa     240
ttgggcccag aaataaaccc ttatttggcc catcttgcta gaatgtataa tggttatgca     300
ggtggatttg aagtgcaggt ggtcctggct gggaatgcgt tcacagcagg aaagataatc     360
tttgcagcta taccccctaa ttttccaatt gataatctga gcgcagcaca aatcactatg     420
tgcccgcatg tgattgtgga tgtcagacag ttggaaccgg tcaaccttcc gatgcctgac     480
gttcgcaaca atttctttca ttacaatcaa gggtctgatt cgcgattgcg cttaattgca     540
atgctgtata cacctcttag ggcaaataat tctggagatg atgttttcac tgtgtcttgt     600
agagtactga ctaggcctag ccctgatttt tcattcaatt ccttgtccc acccaccgtg      660 gaatcaaaga caaaacccctt taccctccct attctgacta tctctgaaat gtccaattct     720
aggtttccag tgccgattga gtcttttgcac accagcccaa ctgagaatat tgttgtccag     780
tgccaaaatg gcgcgtcac tctcgatggt gagttgatgg caccaccca actcttaccg       840 agtcaaattt gtgctttttag gggcgtgctc accagatcaa caagcagggc cagtgatcag     900
gccgatacag caaccccctag ctgtttaat tattattggc atgtacaatt ggataatcta     960
aatgggaccc cttatgatcc tgcagaagac ataccaggcc ccctaggac accagacttc     1020 cggggcaagg tctttggcgt ggccagccag agaaacctcg acagcacaac tagagcacat    1080
gaagcaaaag tggacacaac agctggtcgt ttcacccccaa agttgggctc attagaaata    1140
tctactgatt ccgatgactt tgaccaaaac cagccaacaa agttcacccc agttggcatt    1200
ggggttgaca atgaggcaga atttcagcaa tggtctttac ccgactattc tggtcagttc    1260
acccacaaca tgaacctggc cccagctgtt gctcccaact ccctggtga gcagctcctt    1320 ttcttccgct cacagttacc atcttctggt gggcgatcca acggggtcct agactgtctg    1380 gtccccccagg aatgggtcca acacttctac caggaatcgg ccccgccca acacaagtg    1440 gccctggtta ggtatgtcaa ccctgacact ggtaaagtgc tatttgaggc caagctgcat    1500
aaattaggtt ttatgactat agctaacaat ggtgattctc caataactgt tccccccaaat   1560 ggatatttta ggtttgaatc ttgggtgaac ccctttata cacttgcccc catgggaact    1620
gggaacgggc gtagaaggat tcaataa                                        1647

<210> SEQ ID NO 18
<211> LENGTH: 1623
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
atgaagatgg cgtcgaatga cgctactcca tctaatgatg gtgccgccgg cctcgtgcca      60
gaaagtaaca atgaggcaat ggctctggaa cccgtggtgg gggcgtcttt agccgcccct     120
gtcactggcc aaactaatat aatagacccc tggattagaa ctaattttgt ccaagccccc     180
aatggtgaat ttacagtttc ccctagaaat tcccctggag agatattggt caatttggag     240
ttgggtccag aactgaaccc ttatctggca catttagcta ggatgtacaa tggttatgcg     300
ggtggtatgg aggtgcaagt gatgctcgcg gggaacgcgt tcactgctgg caagatcatc     360
```

| | |
|---|---|
| tttgccgccg tgccacctta ctttccagtg gaaaatctta gcccttccca aataacaatg | 420 |
| ttcccacatg tgatcatcga tgtcagaacc ttggaacctg tattactccc aatgcctgat | 480 |
| gtcagaagca ccctttccca ctttaatcaa aaagatgagc ctaagatgag acttgttgcc | 540 |
| atgctttaca ccccccttcg ttctaatggt tctggtgacg acgttttcac cgtctcatgt | 600 |
| aggatcctca ctaggccctc ccctgaattt gattttacat atttggtgcc accaacagta | 660 |
| gaatcaaaga ctaagccatt cacactacct gtgctgacac tgggagaact gtccaactct | 720 |
| agattccctc tctctattga tgaaatggtc accagcccca atgagtccat agttgttcag | 780 |
| ccacagaatg gtagggtcac actagatggg agctgttag gcacaaccca actgcaagca | 840 |
| tgcaacattt gctccataag ggggaaggta acagggcagg tccctagtga acaacacatg | 900 |
| tggaacctgg agatcacaaa cctaaatggg acgcaatttg accctacaga tgatgtccca | 960 |
| gcccccttg tgtgcccga ctttgcaggt gaggtctttg gtgtactcag ccagagaaat | 1020 |
| agaggtgaaa gcaacccagc aaacagggct catgacgctg tcgtggctac ctacagtgac | 1080 |
| aagtacaccc ctaaactagg cttagtgcaa attggaactt ggaacaccaa tgatgttgaa | 1140 |
| aaccagccaa caaaattcac cccaattggt ttgaatgagg tcgccaatgg ccatcgattt | 1200 |
| gaacagtgga ctttgcctag gtattctggt gccctgacat aaatatgaa tttagcccct | 1260 |
| gctgtggccc cgctctttcc tggagagcgt ctccttttct tccgctctta tgtcccatta | 1320 |
| aaaggtggat ttggaaaccc tgctatagat tgttcggtgc ctcaggagtg ggtccaacat | 1380 |
| ttctatcagg aatctgcccc ttctctgggg gatgtggcct tagttaggta cgtcaaccca | 1440 |
| gacaccgggc gcgtccttt cgaggccaaa ctccacaaag gtgggttcct gactgtgtct | 1500 |
| agtactagca cagggcctgt tgtggttcca gccaatggct atttcaaatt tgattcctgg | 1560 |
| gttaatcaat tttactctct tgcccccatg ggaactggaa atgggcgtag aagggttcag | 1620 |
| taa | 1623 |

<210> SEQ ID NO 19
<211> LENGTH: 1608
<212> TYPE: DNA
<213> ORGANISM: ARTIFICIAL SEQUENCE
<220> FEATURE:
<223> OTHER INFORMATION: SYNTHETIC DNA

<400> SEQUENCE: 19

| | |
|---|---|
| atgaagatgg cgtcgaatga cgccgctcca tctaatgatg gtgcagccgg tcttgtacca | 60 |
| gaggctaaca atgagaccat ggcacttgaa ccggtggctg gggcttcaat agccgcccca | 120 |
| ctcaccggcc aaaacaatat tatagacccc tggattagat taaattttgt gcaggctccc | 180 |
| aatggagagt tcacggtttc accccgcaac tcacccgggg aagtcctatt aaatttggaa | 240 |
| ttaggccccg aactaaatcc atacctagca caccttttcta gaatgtataa tggttatgca | 300 |
| ggtggggttg aggtgcaagt actactggct gggaatgcgt tcacagctgg aaaattggtg | 360 |
| tttgccgcag ttcccctca ttttccatta gaaaacataa gccctggtca gataactatg | 420 |
| ttcctcatg taattattga tgttaggact ttagaaccag ttttgttgcc ccttcctgat | 480 |
| gttaggaata atttctttca ttataatcag cagaatgaac cgaggatgag actcgtagca | 540 |
| atgctttata ctcctcttag atctaatggt tctggtgatg atgtatttac tgtctcctgc | 600 |
| agggtgctta cccgaccttc ccctgattt gattttaatt acttggtccc cctaccctt | 660 |
| gaatctaaaa ctaaaccctt cacactccct atccttgacta taggggagtt aaccaactcc | 720 |
| aggttccctg tgcccataga tgagctctac accagcccca atgagagtct ggtggtgcaa | 780 |

| | |
|---|---:|
| ccccagaacg ggagatgcgc gctagatggg gagctacagg gcacgactca gctcctcccc | 840 |
| acggcgattt gctcgttcag gggccggatc aatcaaaagg tgagtggaga aaaccatgtt | 900 |
| tggaatatgc aggtcaccaa catcaacggg acccctttg atccaacagg ggatgtcccg | 960 |
| gctcctctag gaaccccaga tttctctggc aagctctttg gtgtactaag ccagagagac | 1020 |
| catgataatg cctgtaggag tcatgatgca gtaattgcaa ccaactctgc caaattcact | 1080 |
| ccaaaattgg gcgctataca aattggcaca tgggaagaag acgatgtgca catcaaccaa | 1140 |
| cctactaagt ttactccagt tggcttgttt gaaaatgaag gtttcaacca gtggacactc | 1200 |
| cccaattatt ctggagcctt aacacttaat atggggttgg ccctcctgt ggcccccacc | 1260 |
| ttccctggtg aacaaattct tttctttaga tcccacattc ctcttaaagg aggtgtggcg | 1320 |
| gacccagtta ttgattgtct cttgcctcaa gagtggatcc aacatcttta ccaagagtcg | 1380 |
| gccccttcac aatcagatgt agcattgatt aggtttacaa atccagacac aggacgtgtt | 1440 |
| ctatttgaag caaaattaca caggagtggt tacattacag tggccaatac tggtagcaga | 1500 |
| ccgattgtgg taccagctaa tggttacttc aggtttgata cttgggtcaa tcaattctat | 1560 |
| tctctcgccc ccatgggaac tggaaatggg cgtagaaggg ttcagtaa | 1608 |

```
<210> SEQ ID NO 20
<211> LENGTH: 1629
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
```

| | |
|---|---:|
| atgaagatgg cgtcgaatga cgccgctcca tcaaatgatg gtgcagctag tctcgtacca | 60 |
| gagggcatta atgagactat gccattggaa cccgttgctg gcgcatctat tgctgcccca | 120 |
| gtggcgggac aaaccaacat aattgacccc tggataagaa caatttttgt acaagccccc | 180 |
| aatggagagt ttacagtgtc accaagaaat tcccctggag aaatttttat aaatttagaa | 240 |
| ttaggaccag atctgaatcc ttatttggcc catctttcaa gaatgtacaa tggttatgct | 300 |
| ggaggtgttg aggtgcaagt gctccttgct gggaacgcgt tcacagcagg taagatattg | 360 |
| tttgcagcaa tcccacctaa ctttctcgta gatatgatta gcccagctca aattactatg | 420 |
| cttccccatt tgattgtaga tgttaggact ttggaaccta ttatgacacc cttgcctgat | 480 |
| gttaggaatg tgttctatca tttttaataat caacctcaac ctagaatgag gttagtggct | 540 |
| atgctctaca ccccattgag gtctaatggt tcaggagatg atgtcttcac tgtgtcttgt | 600 |
| agagtactaa ctaggccaac tcctgatttt gaatttattt acctggtgcc cccttctgta | 660 |
| gagtccaaaa ctaaaccatt cacactacca atattaacca tttctgaatt gaccaactcc | 720 |
| cggttcccca ttccaatcga gcaattgtat acggctccaa atgaaaccaa tgttgtccag | 780 |
| tgtcagaatg cagtgcac cttagatgga gagctccagg gcacaaccca gctgttatca | 840 |
| agtgcagttt gcttcttaca gggcaggact gtggctgata atggggataa ttgggaccaa | 900 |
| aatttgctcc agctgaccta tccaaatggt gcaagctatg accccactga tgaagtgcca | 960 |
| gcaccattgg gcactcagga ttttagtggg atgttgtatg gagtgttgac ccaggacaat | 1020 |
| gtgaatgtga gcacaggaga ggccaaaaat gctaagggaa tatacatatc caccactagt | 1080 |
| ggaaaattca ccccaaaaat tgggtcaatt ggattgcatt caataactga gcatgtgcac | 1140 |
| cccaaccaac agtcgcggtt caccccgtc ggagtcgccg tggatgagaa caccccttc | 1200 |
| cagcaatggg ttctgccaca ttatgcaggt agtctcgctc tcaacaccaa tttggcacct | 1260 |

```
gctgttgccc cgactttccc tggtgagcaa ttgctgttct tcaggtcccg tgtcccatgt    1320
gttcaaggcc tacagggaca ggatgcgttc atagattgcc tcctgcccca agagtgggtg    1380
aatcattttt accaagaggc agcccttcc caagcagacg ttgcccttat taggtatgtc    1440
aaccctgata ccggtcgcac gctgtttgaa gccaaattgc atagatcagg tttattact     1500 gtgtcacata ctggtgctta ccctcttgta gtcccccaa atggtcattt caggtttgat     1560
tcttgggtta atcaatttta ctcactcgcc cccatgggaa ctggcaatgg gcgtagaaga    1620
attcagtaa                                                            1629

<210> SEQ ID NO 21
<211> LENGTH: 1653
<212> TYPE: DNA
<213> ORGANISM: ARTIFICIAL SEQUENCE
<220> FEATURE:
<223> OTHER INFORMATION: SYNTHETIC DNA

<400> SEQUENCE: 21
atgaagatgg cgtcgaatga cgctgctcca tcgaatgatg gtgctgccaa cctcgtacca      60
gaggccaacg atgaggttat ggcacttgaa ccggtggtgg gagcctcaat tgcagctcct     120
gttgtcggcc agcaaaatat aattgacccc tggattagag aaaattttgt ccaagcacca    180
caaggtgagt tcactgtttc accaaggaat tcgcctggcg agatgctctt aaaccttgag    240
ttgggcccag aacttaatcc ctatttaagt catttgtccc gcatgtacaa cggatatgct    300
ggtggcatgc aggttcaggt ggtcctagct gggaatgcgt tcacagctgg aaaaatcatc    360
tttgccgccg tgccaccaca tttccctgta gaaaacatca gtgcagccca ataactatg     420 tgtccccatg tgattgttga tgtgagacaa cttgaaccag tgcttctgcc cctcctgat    480 ataaggaata ggttcttcca ctacaaccag gagaacaccc cccggatgag gcttgtagcc    540
atgctctata cacctctaag ggctaactct ggtgaggatg tattcactgt gtcctgcagg    600
gttctgactc gccccgcccc agattttgag ttcacatttt tagttccacc aactgttgaa    660
tcaaaaacaa aaccctttac tttacctatc ttgactcttg gcgagttgtc taattctcgc    720
tttccggctg ctatagatat gctttatact gaccctaatg aatcaatagt tgtacaaccc    780
caaaatggta ggtgcaccct tgatggtaca ttgcaaggca caacacaatt ggttcccaca    840
cagatctgtg ctttttagagg caccctgatc agccagaccg cgagagcggc cgattcaaca    900
gattcccccc agagagcccg taatcatcca ctgcacgtcc aagttaagaa cctagacggt    960
acacaatatg acccaacgga cgatatacct gcagtcctgg gggctattga cttcaaaggt    1020
acagtctttg gagtggctag tcagagggat gtttctggac aacaagaaca gggccactat    1080
gccacccgag cccatgaagc acacatcgac acaactgatc caaagtatgc acccaaatta    1140
ggcacaattc tcattaaatc tggttctgat gatttcaata caaaccagcc cattagattc    1200
actccggtgg gcatgggtga caacaattgg agacaatggg aattgcccga ctattctggc    1260
agattaacct taaatatgaa ccttgctcct gctgtttctc catctttccc tggtgaacga    1320
atccttttct tcaggtccat agtaccatca gccggaggct acgggtctgg ctacatagac    1380
tgtctcatac cccaggaatg ggtgcagcac ttttaccagg aagcagcacc ttcacaatct    1440
gctgttgcac tggttaggta tgtcaacccc gatactgggc gtaacatctt tgaggccaaa    1500
ctgcacagag aagggttcct caccgtggcc aactgtggaa acaatcctat tgtagtcccc    1560
cccaatggct atttcagatt tgaggcttgg ggtaatcagt tttatacact tgcccccatg    1620
ggatctggac aggggcgtag aagggcccag taa                                 1653
```

<210> SEQ ID NO 22
<211> LENGTH: 1626
<212> TYPE: DNA
<213> ORGANISM: ARTIFICIAL SEQUENCE
<220> FEATURE:
<223> OTHER INFORMATION: SYNTHETIC DNA

<400> SEQUENCE: 22

| | | | | | |
|---|---|---|---|---|---|
| atgaagatgg | cgtcgaatga | cgcagctcca | tctagtgatg | gtgcagcagg | cctcgtacca | 60 |
| gagatcaaca | atgaggtcat | gccccttgaa | cccgtggctg | gtgcatcgct | ggcgacacca | 120 |
| gtcgtcgggc | aacaaaatat | aattgatccc | tggataagaa | ataattttgt | gcaggctcct | 180 |
| gcaggtgagt | ttactgtttc | ccctaggaat | tcccctggag | aaattttgct | tgatttggaa | 240 |
| ttgggaccag | atttgaatcc | ctacctagcc | catctggccc | gcatgtataa | tgggcacgct | 300 |
| ggcggcatgg | aagtgcaaat | tgtgctggct | gggaatgcgt | tcacagcagg | caaaatcata | 360 |
| tttgctgcca | tcccccagg | gttcccatat | gaaaatttgt | caccttctca | aattacaatg | 420 |
| tgcccacatg | ttataattga | tgttaggcaa | ttggagccat | tccttttgcc | tatgccagac | 480 |
| atttggaata | atttcttcca | ttataatcag | ggcaatgatc | caaaattgag | gctagttgct | 540 |
| atgctctata | ctcctttgag | ggctaataat | tctggtgatg | atgtgttcac | agtttcttgt | 600 |
| agggtgctca | caaaaccttc | acccgacttt | gaattcacat | ttctagttcc | ccccacagtc | 660 |
| gagtctaaga | ctaagcaatt | cgctctgccc | attctcaaaa | tatcagagat | gactaattca | 720 |
| agattcccag | taccagtgga | tgtgatgtac | acggccagga | acgagaacca | ggtcgtccaa | 780 |
| ccacagaatg | cagggtcac | actcgacggt | gaactgttgg | gcaccactcc | cctgttggct | 840 |
| gttaacatct | gtaaatttaa | gggagaagtc | atagccaaaa | atggggacgt | gagatcctat | 900 |
| agaatggata | tggaaatcac | taacactgat | ggaacaccta | ttgaccccac | agaggacaca | 960 |
| cctggtccca | ttggctcacc | agattttcag | ggcatacttt | ttggcgttgc | cagtcagcgc | 1020 |
| aataagaatg | agcaaaaccc | cgccacgagg | gctcatgaag | ccataattaa | cactggtgga | 1080 |
| gaccatttat | gccccaaat | tagctcaagt | gaaatttatc | tcacaagtcc | caacattttg | 1140 |
| aggtgcacca | cccacaacc | tttaccccag | tcggggttgc | ggggggacaat | tctcatccgt | 1200 |
| tcagacaatg | gacactgcca | cgatatggtg | ggcacctcac | caacaacacc | cacctggccc | 1260 |
| cagcagtggc | gccgctgttc | ccgggggagc | aattgctgtt | cttcaggtca | cagatacccca | 1320 |
| gttccggtgg | tcatgaatcg | cgttacatgg | attgtcttgt | cccacaagag | tgggttcagc | 1380 |
| acttctacca | ggaagctgcc | acagctcaat | ctgaggtggc | ccctcataag | attcatcaac | 1440 |
| ccagacactg | gtagggtcct | ttttgaggct | aggctacata | agcaaggctt | cataactgtg | 1500 |
| gctcataccg | gtgacaaccc | aattgtcatg | ccaccaaatg | ggtatttcag | gtttgaagct | 1560 |
| tgggtcaatc | agttttattc | acttgccccc | gtgggaactg | ggaaagggcg | tagaagggtc | 1620 |
| caataa | | | | | 1626 |

<210> SEQ ID NO 23
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
aatgatgatg gcgtctaagg a  21

```
<210> SEQ ID NO 24
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
tttttttttt tttttttttt tttttttttt ttt                                   33

<210> SEQ ID NO 25
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
gccattatcg gcgcaracca agcc                                             24

<210> SEQ ID NO 26
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 26
tgacctcgga ttgtggacag                                                  20

<210> SEQ ID NO 27
<211> LENGTH: 31
<212> TYPE: DNA
<213> ORGANISM: ARTIFICIAL SEQUENCE
<220> FEATURE:
<223> OTHER INFORMATION: SYNTHETIC DNA

<400> SEQUENCE: 27
gcgaattctt atctacggac accaagccta c                                     31

<210> SEQ ID NO 28
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 28
gtgaatgaag atggcgtcga                                                  20

<210> SEQ ID NO 29
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 29
ccattataat gcacgcctgc gcc                                              23

<210> SEQ ID NO 30
<211> LENGTH: 22
<212> TYPE: DNA
<213> ORGANISM: ARTIFICIAL SEQUENCE
<220> FEATURE:
<223> OTHER INFORMATION: SYNTHETIC DNA
```

-continued

```
<400> SEQUENCE: 30
ttgtgaatga agatggcgtc ga                                              22

<210> SEQ ID NO 31
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 31
aattattgaa tccttctacg cccg                                            24

<210> SEQ ID NO 32
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 32
aattactgaa cccttctacg cccatttc                                        28

<210> SEQ ID NO 33
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 33
ccataactga acccttctac gcc                                             23

<210> SEQ ID NO 34
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 34
atgaagatgg cgtcgaatga cg                                              22
```

US 7,575,753 B2

SRSV DETECTION KIT

TECHNICAL FIELD

This invention relates to a kit for detecting and distinguishing one or more small round structure viruses (hereinafter called "SRSVs") in a specimen.

BACKGROUND ART

SRSVs are a group of causative viruses of human viral gastroenteritis, the discovery of the first one of which goes back to 1972. They are known to cause infantile acute gastroenteritis and also outbreaks of food poisoning or the like among adults and preschool or elementary school children. Due to the inability to proliferate these SRSVs by cell culture and the lack of animal models capable of exhibiting sensitivity thereto, SRSV antigens and anti-SRSV antibodies are hardly available, resulting in a delay in the development of immunoserologic methods for the detection of the viruses.

Under such circumstances, it was succeeded to clone the gene of the Norwalk virus, an SRSV, in 1993, leading to the determination of the base sequence of its complete genomes [JP(PCT) 6-506823 A]. Subsequently, PCR methods which are useful to amplify a part of an RNA polymerase region were developed, and 14 SRSV-related viruses have been found to date. As a result of analyses of about 120 amino acids in these RNA polymerase regions, SRSVs are considered to be roughly differentiated into two genogroups, that is, Genogroup I including the Norwalk virus strain as a prototype and Genogroup II including the Snow Mountain virus strain as a prototype.

As genetic analyses of SRSV-related viruses proceeded, it came to knowledge that substantial diversity exists even in the same genogroup. As a matter of fact, it was found that with an RT-PCR method making use of primers for the genes of the Norwalk virus and Snow Mountain virus strains as the prototypes of the respective genogroups, every SRSV is not detectable and also that it is very difficult to design primers or set RT-PCT conditions for achieving efficient amplification of SRSVs.

In the meantime, antigens were prepared against some of the viruses, such as the Norwalk virus strain and the Snow Mountain strain, by genetic expression, antibodies were obtained, and ELISA-dependent SRSV detection methods making use of such antibodies were also developed. It was, however, still impossible to detect every gastroenteritis-causing SRSV due to the diversity of the SRSVs.

In Japan, on the other hand, SRSVs were designated in 1997 to be causative factors of food poisoning as defined in the Food Sanitation Act so that, if SRSV food poisoning breaks out, determination of its infection route is required. There is accordingly a desire for a method which easily and surely detects and identifies SRSVs in infected subjects' feces or foods.

DISCLOSURE OF THE INVENTION

Accordingly, an object of the present invention is to provide a kit which can easily detect from a specimen an SRSV-related virus known to date and can surely discriminate its serotype and genogroup.

With the foregoing circumstances in view, the present inventors have proceeded with an genetic and immunological investigation on SRSV-related viruses. As a result, it has been found that combined use of antibodies obtained from 11 SRSV-related virus peptides, including newly-found novel virus peptides, can detect most SRSVs in specimens and can surely discriminate the serotypes and genogroups of the SRSVs, leading to the completion of the present invention.

Specifically, the present invention provides an SRSV detection kit comprising all antibodies against SRSV-related virus constituting peptides selected from the following peptide groups (a) to (k), respectively:

(a) a peptide having an amino acid sequence represented by SEQ ID NO: 1 and peptides each having at least 80% of homology with said amino acid sequence, and partial peptides thereof, (b) a peptide having an amino acid sequence represented by SEQ ID NO: 2 and peptides each having at least 80% of homology with said amino acid sequence, and partial peptides thereof, (c) a peptide having an amino acid sequence represented by SEQ ID NO: 3 and peptides each having at least 80% of homology with said amino acid sequence, and partial peptides thereof, (d) a peptide having an amino acid sequence represented by SEQ ID NO: 4 and peptides each having at least 80% of homology with said amino acid sequence, and partial peptides thereof, (e) a peptide having an amino acid sequence represented by SEQ ID NO: 5 and peptides each having at least 80% of homology with said amino acid sequence, and partial peptides thereof, (f) a peptide having an amino acid sequence represented by SEQ ID NO: 6 and peptides each having at least 80% of homology with said amino acid sequence, and partial peptides thereof, (g) a peptide having an amino acid sequence represented by SEQ ID NO: 7 and peptides each having at least 80% of homology with said amino acid sequence, and partial peptides thereof, (h) a peptide having an amino acid sequence represented by SEQ ID NO: 8 and peptides each having at least 80% of homology with said amino acid sequence, and partial peptides thereof, (i) a peptide having an amino acid sequence represented by SEQ ID NO: 9 and peptides each having at least 80% of homology with said amino acid sequence, and partial peptides thereof, (j) a peptide having an amino acid sequence represented by SEQ ID NO: 10 and peptides each having at least 80% of homology with said amino acid sequence, and partial peptides thereof, and (k) a peptide having an amino acid sequence represented by SEQ ID NO: 11 and peptides each having at least 80% of homology with said amino acid sequence, and partial peptides thereof.

The present invention also provides an SRSV detection kit for discriminating SRSVs in genogroup, said SRSV detection kit comprising all antibodies against SRSV-related virus constituting peptides selected from the following peptide groups (a) to (d), respectively:

(a) a peptide having an amino acid sequence represented by SEQ ID NO: 1 and peptides each having at least 80% of homology with said amino acid sequence, and partial peptides thereof, (b) a peptide having an amino acid sequence represented by SEQ ID NO: 2 and peptides each having at least 80% of homology with said amino acid sequence, and partial peptides thereof, (c) a peptide having an amino acid sequence represented by SEQ ID NO: 3 and peptides each having at least 80% of homology with said amino acid sequence, and partial peptides thereof, and (d) a peptide having an amino acid sequence represented by SEQ ID NO: 4 and peptides each having at least 80% of homology with said amino acid sequence, and partial peptides thereof.

Further, the present invention also provides an SRSV detection kit for discriminating genogroup of SRSVs, said SRSV detection kit comprising all antibodies against SRSV-related virus constituting peptides selected from the following peptide groups (e) to (k), respectively:

(e) a peptide having an amino acid sequence represented by SEQ ID NO: 5 and peptides each having at least 80% of homology with said amino acid sequence, and partial peptides thereof, (f) a peptide having an amino acid sequence represented by SEQ ID NO: 6 and peptides each having at least 80% of homology with said amino acid sequence, and partial peptides thereof, (g) a peptide having an amino acid sequence represented by SEQ ID NO: 7 and peptides each having at least 80% of homology with said amino acid sequence, and partial peptides thereof, (h) a peptide having an amino acid sequence represented by SEQ ID NO: 8 and peptides each having at least 80% of homology with said amino acid sequence, and partial peptides thereof, (i) a peptide having an amino acid sequence represented by SEQ ID NO: 9 and peptides each having at least 80% of homology with said amino acid sequence, and partial peptides thereof, (j) a peptide having an amino acid sequence represented by SEQ ID NO: 10 and peptides each having at least 80% of homology with said amino acid sequence, and partial peptides thereof, and (k) a peptide having an amino acid sequence represented by SEQ ID NO: 11 and peptides each having at least 80% of homology with said amino acid sequence, and partial peptides thereof.

Furthermore, the present invention also provides SRSV-related virus strain genes having base sequences represented by SEQ ID NOS: 15, 20, 21 and 22 or base sequences similar to the first-mentioned base sequences, respectively, except for deletion, replacement or addition of one to several bases of said first-mentioned base sequences.

BEST MODES FOR CARRYING OUT THE INVENTION

1. SRSV-related Viruses

Figure 1:
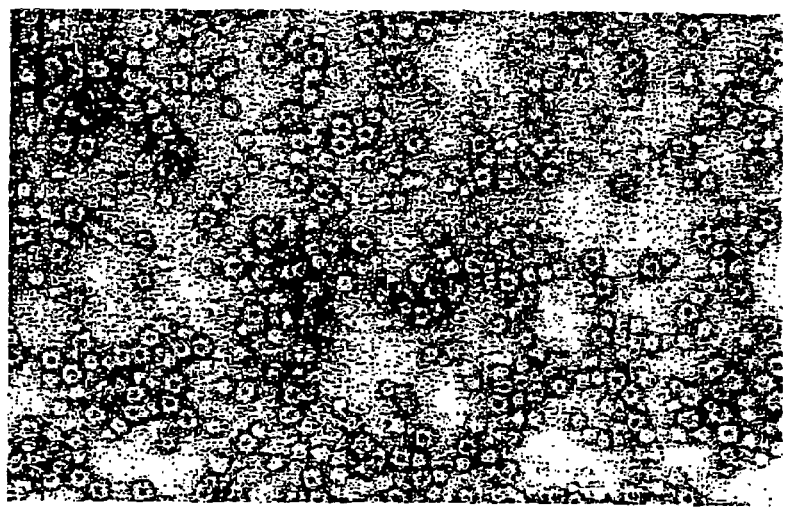
FIG. 1 is an electron micrograph (×100,00) of virus-like particles derived from the Hu/NLV/Seto 124/1989/JP strain.

The SRSV detection kit according to the present invention is characterized by the use of the antibodies against SRSV-related virus constituting peptides having the 11 specific amino acid sequences or at least 80% of homologies with the amino acid sequences in the groups (a) to (k). Of these, the peptides belonging to the group (d), the group (i), the group (j) and the group (k) are novel peptides different from any SRSV-related viruses registered with the GeneBank to date (Table 1, which will be described subsequently herein). Owing to the incorporation of the 11 antibodies, including antibodies against these novel peptides, into the kit, SRSV-related viruses can be detected without omission.

The SRSV-related virus constituting peptides useful in the present invention embrace their mutants in each of which one or more amino acids have been deleted from, replaced in or added to its corresponding amino acid sequence; and also their mutants in each of which one or several bases have been deleted from, replaced in or added to a base sequence encoding its corresponding amino acid sequence.

Illustrative of the peptide having the amino acid sequence represented by the SEQ ID NO: 1 in the group (a) is a virus constituting peptide of the Hu/NLV/Kashiwa 645/1999/JP strain obtained from feces of an SRSV infected patient in Japan, whereas examples of the peptides each having at least 80% of homology with the amino acid sequence include one derived from the Desert Shield/90/SA strain (GeneBank Accession No. U04469).

Illustrative of the peptide having the amino acid sequence represented by the SEQ ID NO: 2 in the group (b) is a virus constituting peptide of the Hu/NLV/Seto 124/1989/JP strain obtained from feces of an SRSV infected patient in Japan, whereas examples of the peptides each having at least 80% of homology with the amino acid sequence include those derived from the KY-89/89J strain (GeneBank Accession No. L23828) and the Norwalk/68/US strain (GeneBank Accession No. M876611).

Illustrative of the peptide having the amino acid sequence represented by the SEQ ID NO: 3 in the group (c) is a virus constituting peptide of the Hu/NLV/Funabashi 258/1996/JP strain obtained from feces of an SRSV infected patient in Japan, whereas examples of the peptides each having at least 80% of homology with the amino acid sequence include one derived from the Southampton/91/UK strain (GeneBank Accession No. L07418).

Illustrative of the peptide having the amino acid sequence represented by the SEQ ID NO: 4 in the group (d) is a virus constituting peptide of the Hu/NLV/Chiba 407/1987/JP strain obtained from feces of an SRSV infected patient in Japan.

The peptide having the amino acid sequence represented by SEQ ID NO: 4 has less than 75% of homology in structural gene (SEQ ID NO: 15) with any one of the SRSV-related virus strains (Table 1, which will be described subsequently herein) registered with the GeneBank to date, and is a peptide having a novel sequence not reported to date.

Illustrative of the peptide having the amino acid sequence represented by the SEQ ID NO: 5 in the group (e) is a virus constituting peptide of the Hu/NLV/Narita 104/1997/JP strain obtained from feces of an SRSV infected patient in Japan, whereas examples of the peptides each having at least 80% of homology with the amino acid sequence include those derived from the Bristol/93/UK strain (GeneBank Accession No. X76716), the Lordsdale/93/UK strain (GeneBank Accession No. X86557), and the Camberwell/94/AU strain (GeneBank Accession No. U46500).

Illustrative of the peptide having the amino acid sequence represented by the SEQ ID NO: 6 in the group (f) is a virus constituting peptide of the Hu/NLV/Sanbu 809/1998/JP strain obtained from feces of an SRSV infected patient in Japan, whereas examples of the peptides each having at least 80% of homology with the amino acid sequence include those derived from the Mexico/89/MEX strain (GeneBank Accession No. U22498), the Auckland strain (GeneBank Accession No. U460391), the Toronto/77/CA strain (GeneBank Accession No. U02030), and the OTH-25/89/J strain (GeneBank Accession No. L23830).

Illustrative of the peptide having the amino acid sequence represented by the SEQ ID NO: 7 in the group (g) is a virus constituting peptide of the Hu/NLV/Ichikawa 754/1998/JP strain obtained from feces of an SRSV infected patient in Japan, whereas examples of the peptides each having at least 80% of homology with the amino acid sequence include those derived from the Snow Mountain/76/US strain (GeneBank Accession No. U70059) and the Melksham/89/UK strain (GeneBank Accession No. X81879).

Illustrative of the peptide having the amino acid sequence represented by the SEQ ID NO: 8 in the group (h) is a virus constituting peptide of the Hu/NLV/Chitta 1876/1996/JP strain obtained from feces of an SRSV infected patient in Japan, whereas examples of the peptides each having at least 80% of homology with the amino acid sequence include one derived from the Hawaii/71/US strain (GeneBank Accession No. U07611).

Illustrative of the peptide having the amino acid sequence represented by the SEQ ID NO: 9 in the group (i) is a virus constituting peptide of the Hu/NLV/Kashiwa 47/1997/JP strain obtained from feces of an SRSV infected patient in Japan.

The peptide having the amino acid sequence represented by SEQ ID NO: 9 has less than 75% of homology in structural gene (SEQ ID NO: 20) with any one of the SRSV-related virus strains (Table 1, which will be described subsequently herein) registered with the GeneBank to date, and is a peptide having a novel sequence not reported to date.

Illustrative of the peptide having the amino acid sequence represented by the SEQ ID NO: 10 in the group (j) is a virus constituting peptide of the Hu/NLV/Mie 7 k/1994/JP strain obtained from feces of an SRSV infected patient in Japan.

The peptide having the amino acid sequence represented by SEQ ID NO: 10 has less than 70% of homology in structural gene (SEQ ID NO: 21) with any one of the SRSV-related virus strains (Table 1, which will be described subsequently herein) registered with the GeneBank to date, and is a peptide having a novel sequence not reported to date.

Illustrative of the peptide having the amino acid sequence represented by the SEQ ID NO: 11 in the group (k) is a virus constituting peptide of the Hu/NLV/Osaka 10-25/1999/JP strain obtained from feces of an SRSV infected patient in Japan.

The peptide having the amino acid sequence represented by SEQ ID NO: 11 has less than 70% of homology in structural gene (SEQ ID NO: 22) with anyone of the SRSV-related virus strains (Table 1, which will be described subsequently herein) registered with the GeneBank to date, and is a peptide having a novel sequence not reported to date.

TABLE 1

| Virus strain | GeneBank Accession No. |
| --- | --- |
| Desert Shield/90/SA | U04469 |
| Norwalk/68/US | M876611 |
| KY-89/89J | L23828 |
| OTH-25/89/J | L23830 |
| Southampton/91/UK | L07418 |
| Lordsdale/93/UK | X86557 |
| Bristol/93/UK | X76716 |
| Camberwell/94/AU | U46500 |
| Toronto/77/CA | U02030 |
| Mexico/89/MEX | U22498 |
| Snow Mountain/76/US | U70059 |
| Melksham/89/UK | X81879 |
| Auckland | U460391 |
| Hawaii/71/US | U07611 |

The SRSV-related virus constituting peptides in these groups (a) to (k) embrace, in addition to the above-described peptides, partial peptides each of which contains a specific amino acid sequence in its corresponding peptide and has antigenecity equivalent to the corresponding peptide.

According to a homological analysis of about 120 amino acids of RNA polymerase regions of the SRSV-related virus constituting peptides, these SRSV-related virus constituting peptides can be classified into two genogroups. Described specifically, they can be classified into Type I to which the peptides in the groups (a) to (d) belong and Type II to which the peptides in the groups (e) to (k) belong.

2. Cloning of the SRSV-related Virus Constituting Genes

From feces of an SRSV infected patient, viral RNA is extracted using the cetyltrimethylammonium bromide (CTAB) method or the like, cDNA was formed by an oligo-dT primer and a reverse transcriptase, and using the cDNA and primers capable of amplifying structural gene regions of the individual SRSV-associate viruses, PCR was conducted to amplify structural gene fragments.

Such a structural gene fragment is inserted in a plasmid by once conducting TA cloning with an *E. coli* cloning vector.

As a cloning vector usable here, it is possible to use a known cloning vector such as a vector derived from a plasmid obtained using as host procaryotic cells represented by *E. coil* or from a bacteriophage represented bye phage, and appropriately combined use of a cloning vector and its host cell is desired. Specific examples of the cloning vector include pBR322, pUC19 and pCRII. The insertion of the DNA can be conducted by a method known per se in the art, and upon formation of such a vector, use of *E. coli* cells is desired as they permit easy genetic manipulation.

3. Expression of Structural Gene and Creation of Virus-like Particles.

By having fragments of the above-obtained individual virus constituting genes in the groups (a) to (k) expressed with a suitable expression system or by using virus-like particles created from the virus constituting peptides in a genetic engineering manner, antibodies against the respective viruses can be obtained. A description will hereinafter be made about an expression when *E. coli* is used and also about the creation of virus-like particles.

(1) Expression by *E. coli*

Plasmids with the structural gene regions of the respective SRSV-related viruses incorporated therein, respectively, are each digested with a restriction endonuclease which does not cleave the structural gene region. Then, the structural gene region is collected and incorporated, for example, in pGEX (GST fusion protein expression vector; product of Pharmacia AB), pTrc99A (*E. coli* expression vector; product of Pharmacia AB), pTrxFus (thioredoxin fusion protein expression vector; product of Invitrogen Corporation), pET (expression vector making use of pT7RNA promoter; product of Novagen Inc.), a maltose binding protein expression vector, or a â galactosidase fusion protein expression vector. At this time, the structural gene region to be incorporated can be of the complete length or can be a partial region, with a partial region containing at least one antigen epitope of an SRSV being preferred. Gene expression vectors with the structural gene regions incorporated therein as described above are transformed by an *E. coli* strain suited for gene expression, for example, the BL21 strain, the DH10B strain, the JM109 strain or the XL1-Blue strain. Expression of the gene can be conducted by culturing the thus-obtained transformants in a general liquid culture medium, for example, L-broth. It is preferred for the expression to add a gene expression promoter, for example, IPTG or, when a PL promoter is used, to apply a heat shock.

Purification of a peptide so expressed can be conducted following a general purification method for expressed protein, which makes use of *E coli*. If the expressed protein is in a dissolved form, for example, its purification can be conducted by affinity chromatography making use of a GST column or a column for maltose binding proteins. If the expressed protein is in an insoluble form, its purification can be achieved by conducting affinity chromatography making use of a Ni chelate.

(2) Creation of SRSV Virus-like Particles

A plasmid with a structural gene region of an SRSV-related virus incorporated therein is digested with a restriction endonuclease which does not cleave the structural gene region. Then, the structural gene region is collected and incorporated, for example, in a baculovirus transfer vector such as pVL1393. The transfer vector and a linear baculovirus DNA, from which a gene region essential for proliferation has been deleted, are subjected to transfection in insect cells such that homologous recombination is induced to form the target recombinant baculovirus.

By infecting the thus-obtained recombinant baculovirus to insect cells such as Sf9 cells or Tn5 cells and incubating the infected insect cells under adequate growth conditions in a manner known per se in the art, the structural protein of the SRSV is expressed. By allowing the structural protein to undergo self-assembly, virus-like particles can be produced. Use of a biochemical purification method, for example, centrifugation makes it possible to isolate and purify the virus-like particles. Whether or not such virus-like particles have been formed can be confirmed by subjecting the self-assembled product to negative staining with uranyl acetate and examining the stained self-assembled product by an electron microscope.

The virus-like particles obtained as described above do not have infectiveness as they do not contain any gene internally. Nonetheless, they have antigenecity equivalent to virus particles because they structurally have substantially the same shape as virus particles.

4. Acquisition of Antibodies against SRSV-related Viruses

By immunizing an animal with the thus-obtained virus constituting peptide or virus-like particles, an anti-SRSV-related virus antibody can be prepared. Incidentally, such an antibody can be either a monoclonal antibody or a polyclonal antibody.

Preparation of an immune antibody by making use of virus-like particles can be conducted, for example, as will be described next. In a manner known per se in the art, a rabbit is immunized with virus-like particles of one of the SRSV-related viruses, and from separated serum, an IgG antibody (anti-SRSV antibody) against the virus-like particles can be obtained. For the separation and isolation of the antibody, a method such as DEAE Sepharose chromatography can be used.

Using the 11 types of virus-like particles of the groups (a) to (k) obtained as described above and their corresponding anti-SRSV antibodies, their cross reactivities were measured. As will be shown below in Table 2, absolutely no cross-reactivity was exhibited between the individual SRSV-related viruses. According to the SRSV detection method of the present invention, it is therefore possible to concurrently discriminate the serotypes of 11 types of SRSVs. This also indicates the possibility of discriminating Genogroup I Genogroup II from each other at the same time.

5. Detection of SRSV-related Viruses

For the detection of one or more SRSVs in a specimen by the individual anti-SRSV antibodies obtained as described, conventionally employed immunoassays making use of antigen-antibody reactions, for example, radioimmunoassay by the sandwich technique, enzyme-linked immunosorbent assay (ELISA) and the like can be used, with ELISA being particularly preferred. Described specifically, the 11 types of anti-SRSV antibodies are separately poured into a microplate to prepare an SRSV screening plate. A dilution of a fecal emulsion, which has been prepared from feces of an SRSV infected patient, is added to the wells of the plate, and is then allowed to react. Peroxidase (POD) labeled anti-SRSV antibodies of the respective viruses are thereafter added and reacted. After a substrate solution (TMB containing hydrogen peroxide) is added and reacted, 0.6 N sulfuric acid is added to stop the reactions. By measuring the absorbance (450 nm/630 nm) of each well by an ELISA autoreader, the SRSV or SRSVs can be detected.

When it is desired to conduct only the detection of one or more SRSVs in a specimen, a detection kit can be prepared by using a microplate with all the 11 types of anti-SRSV antibodies mixed and immobilized thereon. To also discriminate even the serotypes of the one or more SRSVs, a detection kit can be prepared by using microplates with all the 11 types of anti-SRSV antibodies immobilized separately thereon.

Further, the discrimination of the genogroups is feasible by a kit making use of a microplate with antibodies against the peptides in the groups (a) to (d) mixed and immobilized thereon (Type I plate) or a microplate with antibodies against the peptides in the groups (e) to (k) mixed and immobilized thereon (Type II plate).

Moreover, immobilization of the individual anti-SRSV antibodies useful in the present invention with a carrier such as a latex or magnetic beads makes it possible to surely capture one or more SRSV-related viruses in a specimen. The carrier with one or more SRSV-associate viruses captured thereon can be recovered by centrifugation in the case of the latex or by magnet in the case of the magnetic beads. Subsequent to the recovery, virus RNAs can be extracted and used.

EXAMPLES

The SRSV detection kits according to the present invention will hereinafter be specifically described based on Examples.

Example 1

Cloning of Structural Genes of SRSV-Related Viruses (1) Synthesis of cDNA

PBS (9 mL) and "Daiflon" (1 mL) were added to feces (0.5 to 1.0 g) of an SRSV patient, followed by homogenization. The homogenate was then centrifuged at 3,000 rpm for 20 minutes, and the supernatant was collected as a 10% fecal emulsion.

Using a 1-mL aliquot of the fecal emulsion, RNA of the SRSV was extracted by the cetyltrimethylammonium bromide (CTAB) method, and the RNA was eventually suspended in a 0.1% diethyl pyrocarbonate solution (30 iL). Using the suspension, cDNA was prepared by a reverse transcriptase derived from the Oligo-dT(12-18) primer and AMV (Avian Myeloblastosis Virus) (product of SEIKAGAKU CORPORATION).

(2) Isolation of Structural Gene Regions

Using the cDNA prepared in (1) and primers for amplifying the structural gene regions shown below, PCR was conducted. Subsequent to the PCR, amplified structural gene fragments were separated by agarose gelelectrophoresis, and were then recovered by using "SuprecTM-01" (TAKARA).

Hu/NLV/Kashiwa 645/1999/JP gene:G1/F2(SEQ ID NO: 23), Oligo-dT(33) (SEQ ID NO: 24)

Hu/NLV/Seto 124/1989/JP gene:G1/F2(SEQ ID NO: 23), G1/R0 (SEQ ID NO: 25)

Hu/NLV/Funabashi 258/1996/JP gene:G1/F2(SEQ ID NO: 23), Oligo-dT(33) (SEQ ID NO: 24)

Hu/NLV/Chiba 407/1987/JP gene:D5(SEQ ID NO: 26), CV-U4 (SEQ ID NO: 27)

Hu/NLV/Narita 104/1997/JP gene:97 k104/F1(SEQ ID NO: 28), 97 k104/R1(SEQ ID NO: 29)

Hu/NLV/Sanbu 809/1998/JP gene:G2/F3(SEQ ID NO: 30), MV-R1(SEQ ID NO: 31)

Hu/NLV/Ichikawa 754/1998/JP gene:G2/F3(SEQ ID NO: 30), SMV-R1(SEQ ID NO: 32)

Hu/NLV/Chitta 1876/1996/JP gene:G2/F3(SEQ ID NO: 30), G2/R0 (SEQ ID NO: 33)

Hu/NLV/Kashiwa 47/1997/JP gene:97 k104/F1(SEQ ID NO: 28), Oligo-dT(33) (SEQ ID NO: 24)

Hu/NLV/Mie 7 k/1994/JP gene:G2/F3(SEQ ID NO: 30), Oligo-dT(33) (SEQ ID NO: 24)

Hu/NLV/Osaka 10-25/1999/JP gene:GFCR7 (SEQ ID NO: 34), Oligo-dT(33) (SEQ ID NO: 24)

(3) Cloning of Structural Genes

TA cloning of the recovered structural gene fragments to an E. coli cloning vector, pCRII(product of Invitrogen Corporation) was conducted. Obtained from these clones were plasmids with the structural genes of the viruses incorporated therein, pCRII/645, pCRII/124, pCRII/258, pCRII/Chiba, pCRII/104, pCRII/809, pCRII/754, pCRII/76, pCRII/47, pCRII/7 k, and pCRII/10-25.

Example 2

Determination of Base Sequences

Determination of the base sequences of the structural genes of the Hu/NLV/Kashiwa 645/1999/JP strain, the Hu/NLV/Seto 124/1989/JP strain, the Hu/NLV/Funabashi 258/1996/JP strain, the Hu/NLV/Chiba 407/1987/JP strain, the Hu/NLV/Narita 104/1997/JP strain, Hu/NLV/Sanbu 809/1998/JP strain, the Hu/NLV/Ichikawa 754/1998/JP strain, the Hu/NLV/Chitta 1876/1996/JP strain, the Hu/NLV/Kashiwa 47/1997/JP strain, the Hu/NLV/Mie 7 k/1994/JP strain, and the Hu/NLV/Osaka 10-25/1999/JP strain was conducted in the below-described manner.

Firstly, a primer (first primer) was set in the vicinity of the polyhedrin promoter of pVL1393 as a transfer vector, and by the dye termination method, a labeling reaction was conducted by using a "Cycle Sequencing Kit FS" (product of Perkin-Elmer Corp.). The DNA concentration of the transfer vector employed was 0.4 ig/iL, whereas the concentration of the sequencing primer used was 3.2 pmol/iL. Subsequent to the reaction, the excess fluorescent pigment was eliminated using acentriprep spin column (manufactured by Perkin-Elmer Corp.). The reaction mixture was completely dried by a vacuum lyophilizer, and the lyophilizate was suspended in a special sample buffer (20 iL; product of Perkin-Elmer Corp.). Subsequent to stirring, the suspension was subjected to centrifugal precipitation. The precipitate was dried at 95° C. for 2 minutes. After quenching, it was analyzed by an autosequencer ("ABI Genetic Analyzer 310").

Using the base sequence determined by the first primer, a new sequencing primer (second primer) was set on the 3'-side of the base sequence. Using this second primer, a labeling reaction was conducted by a cyclic sequencing kit in a similar manner as mentioned above. Subsequent to the reaction, operation similar to that mentioned above was performed, and the base sequence was analyzed by the autosequencer. As has been described above, a sequencing primer was set on the 3' side of the base sequence determined in each cycle, and determination of the base sequence was conducted. By repeating this procedure, the base sequences from the 5'-ends to the 3'-ends of the 11 types of SRSV-related virus structural genes (SEQ ID NO: 12 to SEQ ID NO 22) were determined. Among these, the base sequences represented by SEQ ID NO: 15 (the Hu/NLV/Chiba 407/1987/JP strain), SEQ ID NO: 20 (the Hu/NLV/Kashiwa 47/1997/JP strain), SEQ ID NO: 21 (the Hu/NLV/Mie 7 k/1994/JP strain) and SEQ ID NO: 22 (the Hu/NLV/Osaka 10-25/1999/JP strain) were confirmed to be novel sequences not reported to date.

Example 3

Creation of Recombinant Baculovirus Capable of Yielding Virus-Like Particles (1) Construction of Transfer Vectors The plasmids with the structural gene regions incorporated therein, which had been obtained in Example 1(3), were digested by a restriction endonuclease which does not cleave the structural gene regions. Subsequent to separation by agarose gel electrophoresis, the structural gene regions were recovered by "SuprecTM01" (TAKARA). The recovered gene fragments were incorporated in baculovirus transfer vectors pVL1393 (product of Invitrogen Corporation), which had been digested by the same restriction endonuclease, to prepare transfer vectors.

(2) Creation of Recombinant Baculoviruses

Baculovirus DNA (0.5 ig; "Baculo-Gold") and one of the transfer vectors (1 ig) obtained in (1) were dissolved in distilled water (8 iL). The resulting solution was mixed with a two-fold dilution of lipofectin (equivalent amount), and the thus-obtained mixture was left over at room temperature for 15 minutes. After Sf9 cells ($1\times10^5$ cells) suspended in an insect cell culture medium, "Ex-cell 400", were adsorbed at 26.5° C. for 30 minutes in a plastic Petri dish (diameter: 3.5 cm), a mixture of the transfer vector and "Baculo-Gold" was added dropwise to the cells, followed by incubation at 26.5° C. 24 Hours later, the culture medium was replaced by a "TC100" (product of GIBCO BRL Life Technologies; hereinafter referred to as "TC100") which contained 10% fetal bovine serum and 2% BTB (products of GIBCO BRL Life Technologies), and incubation was continued further.

(3) Purification of Recombinant Baculoviruses

After each recombinant baculovirus obtained in (2) was incubated for 5 days, the culture supernatant was diluted tenfold with an insect cell culture medium such as TC100. A 0.1-mL aliquot of the diluted supernatant was taken, and inoculated to $3\times10^6$ Sf9 cells cultured in a plastic Petri dish of 3.5 cm in diameter. Subsequent to adsorption at 26.5° C. for 60 minutes, TC100 culture medium (2 mL) which contained 1% of Agarose ME (low melting-point agarose) was overlayed, followed by incubation at 26.5° C. On the 4$^{th}$ day after the initiation of the incubation, TC100 (1 mL) which contained 0.005% of neutral red was further overlayed, followed by incubation at 26.5° C. On the following day, the formed plaques were scraped off with a microtip. and were suspended in TC100 culture medium.

(4) Production of Recombinant Baculovirus Seeds and Measurement of their Infective Potencies Each suspension obtained in (3) was inoculated to $1\times10^7$ Sf9 cells. Subsequent to adsorption at 26.5° C. for 60 minutes, TC100 was added, followed by incubation at 26.5° C. for 3 to 4 days. The culture was centrifuged at 2,500 rpm for 10 minutes at 4° C., and the culture supernatant was collected. The collected culture supernatant was inoculated to $1\times10^7$ Sf9 cells. Subsequent to adsorption at 26.5° C. for 60 minutes, TC100 was added, followed by incubation at 26.5° C. for 3 to 4 days.

Next, the culture supernatant was inoculated to $3\times10^7$ Sf9 cells cultured in a plastic Petri dish of 3.5 cm in diameter. Subsequent to adsorption at 26.5° C. for 60 minutes, TC100 culture medium (2 mL) which contained 1% of Agarose ME (low melting-point agarose) was overlayed, followed by incubation at 26.5° C. On the 4$^{th}$ day after the initiation of the incubation, TC100 (1 mL) which contained 0.005% of neutral red was then overlayed, followed by incubation at 26.5° C. On the following day, the formed plaques were measured to calculate the infective potency of the recombinant baculovirus. This was recorded as the infective potency of the recombinant baculovirus.

Example 4

Creation of Virus-Like Particles (1) Expression of Structural Proteins by using Recombinant Baculoviruses Each recombinant baculovirus was infected at M.O.I.s (Multiplicities of infection) of 1 to 10 to Sf9 insect cells. Upon infection, a suspension of the recombinant baculovirus was added dropwise to the cells, and the recombinant baculovirus was subjected to adsorption for about 60 minutes or so with gentle shaking. After that, TC100 was added as an insect cell culture medium, followed by incubation at 26.5° C. for 5 to 6 days.

(2) Identification of Expressed Proteins

The culture supernatant of each recombinant virus infection was periodically sampled. After having been resolved by SDS-PAGE, the protein was detected by Coomassie blue staining, and by an expected molecular weight, the validity of the expressed protein was confirmation. Further, subsequent to resolving the protein by SDS-PAGE, the protein was transferred onto a nitrocellulose membrane, and by the Western blotting technique, the expressed protein was then identified with a convalescent serum of the SRSV.

(3) Purification and Recovery of Virus-like Particles

The recombinant baculovirus seeds were infected at M.O.I.s of from 1 to 10. Subsequent to adsorption for about 60 minutes, "Ex-cell 400" was added, followed by incubation at 26.5° C. for 3 days. A protease inhibitor, for example, pepstatin A or a leupeptin, was then added to the culture to a final concentration of 1 mM, followed by further incubation for 2 to 3 days.

Subsequent to the incubation, the culture was centrifuged at 2,500 rpm for 10 minutes at 4° C. to collect the culture supernatant. The collected culture was centrifuged at 10,000 rpm for 30 minutes to eliminate the recombinant baculovirus. The supernatant was centrifuged at 25,000 rpm for 4 hours on a "Beckmann SW28 Rotor" to have virus-like particles precipitated. Then, the centrifuge tube from which the supernatant had been discarded was held upside down to complete eliminate the supernatant. After that, Grace buffer or PBS(−) (0.5 mL) with the protease inhibitor added therein was added to the centrifuge tube, and the centrifuge was allowed to stand overnight at 4° C.

After the standing, the virus-like particles were suspended in the protease-inhibitor-containing Grace buffer which had been added, and were recovered. To the recovered virus-like particles, protease-inhibitor-containing Grace buffer or PBS (−) with CsCl (3.8 g) added therein was added to give 13 mL. The resulting mixture was ultracentrifuged at 16° C. and 35,000 rpm for 24 to 48 hours. Subsequent to the ultracentrifugation, a pale band in which virus-like particles gathered was collected. After 5-fold dilution with protease-inhibitor-containing Grace buffer, the resultant suspension was ultracentrifuged at 45,000 rpm for 3 hours on a "Beckmann TL100.3 Rotor" to have the virus-like particles precipitated.

The precipitated virus-like particles were solubilized with Grace buffer or PBS(−) to which the protease inhibitor had been added. Protease-inhibitor-containing Grace buffer solutions which contained 10% to 50% of sucrose were prepared in a 4PA tube, into which the solubilized solution of the virus-like particles was overlayed, followed by sucrose density-gradient centrifugation at 35,000 rpm for 4 hours at 4° C. Subsequent to the centrifugation, a pale band of virus-like particles was collected as purified SRSV virus-like particles in a 1-mL syringe fitted with a 26 G needle.

The purified SRSV virus-like particles was diluted with Grace buffer as needed, and the quantity of protein was measured by the Bradford method.

Figure 2:
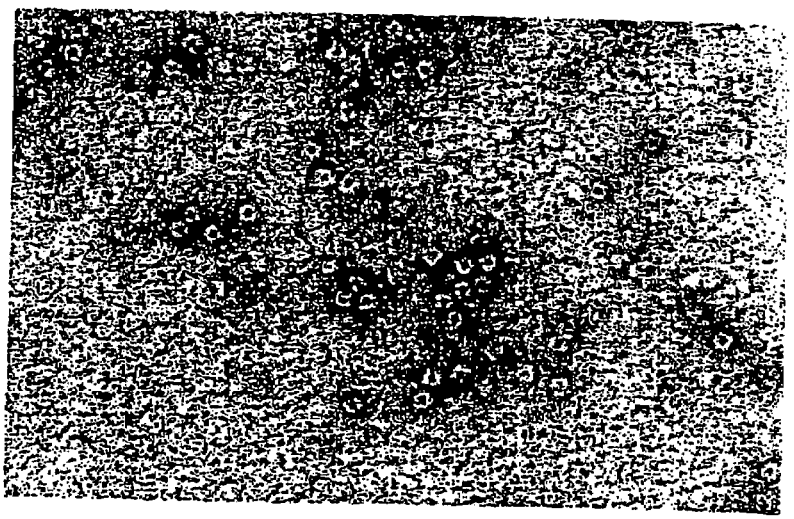
FIG. 2 is an electron micrograph (×100,00) of virus-like particles derived from the Hu/NLV/Funabashi 258/1996/JP strain.
Figure 3:
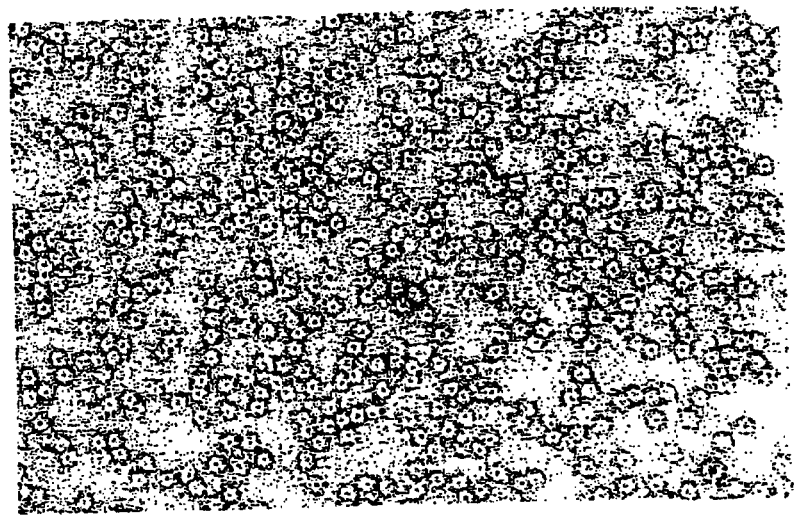
FIG. 3 is an electron micrograph (×100,00) of virus-like particles derived from the Hu/NLV/Chiba 407/1987/JP strain.
Figure 4:
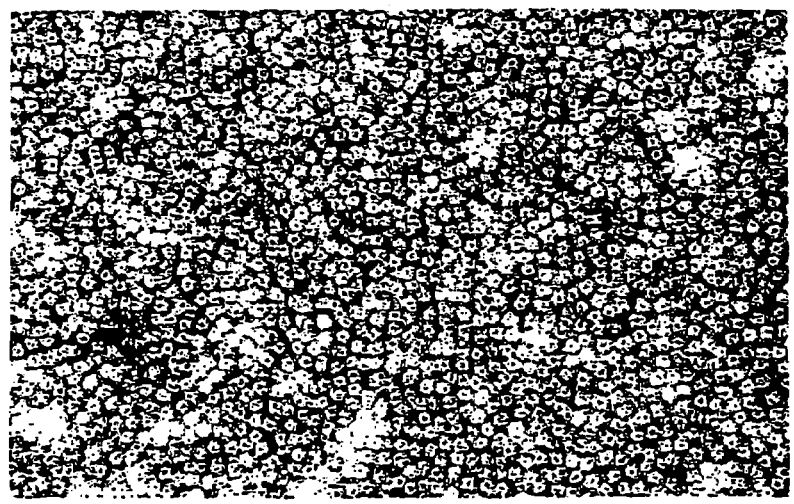
FIG. 4 is an electron micrograph (×100,00) of virus-like particles derived from the Hu/NLV/Narita 104/1997/JP strain.
Figure 5:
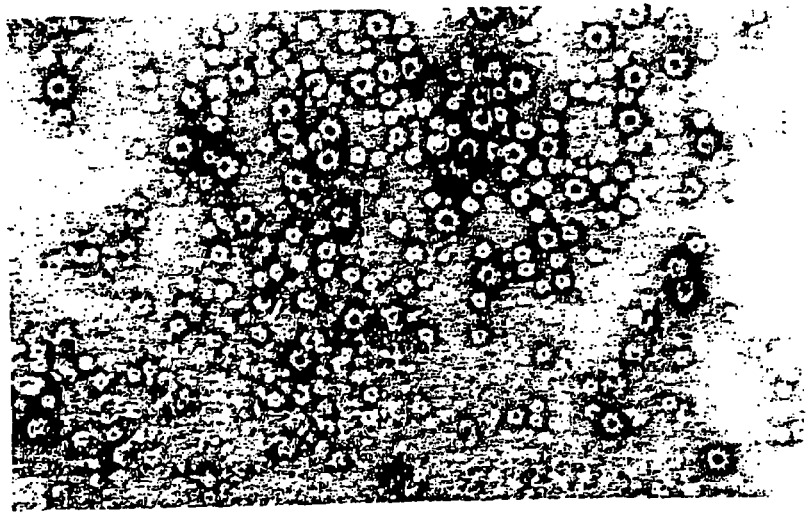
FIG. 5 is an electron micrograph (×100,00) of virus-like particles derived from the Hu/NLV/Sanbu 809/1998/JP strain.
Figure 6:
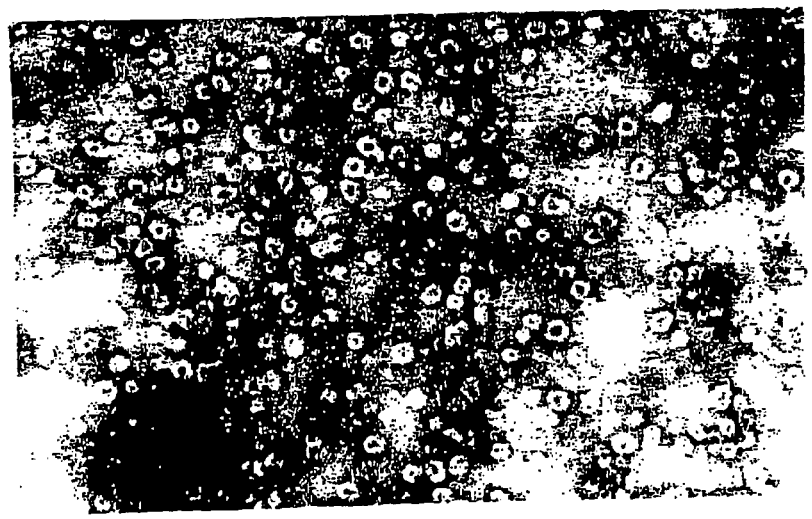
FIG. 6 is an electron micrograph (×100,00) of virus-like particles derived from the Hu/NLV/Ichikawa 754/1998/JP strain.
Figure 7:
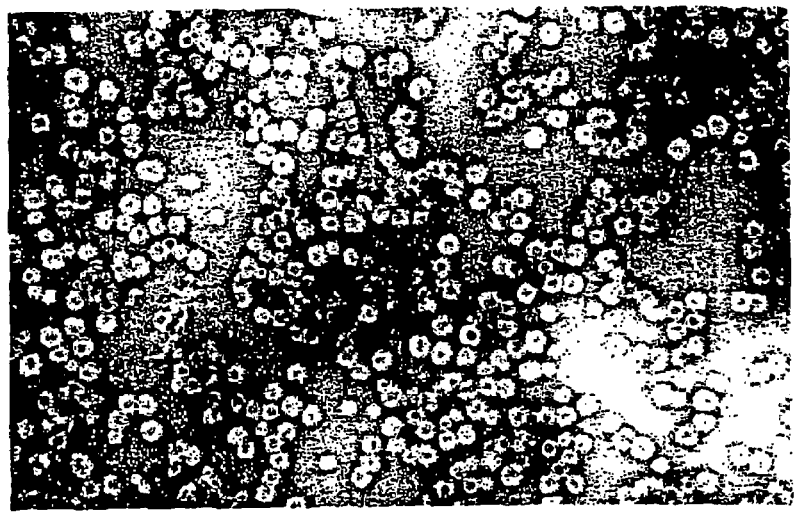
FIG. 7 is an electron micrograph (×100,00) of virus-like particles derived from the Hu/NLV/Chitta 1876/1996/JP strain.
Figure 8:
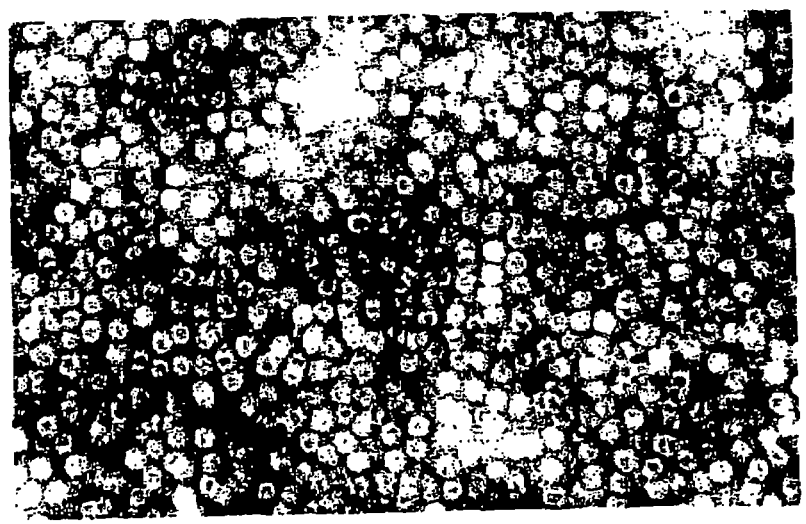
FIG. 8 is an electron micrograph (×100,00) of virus-like particles derived from the Hu/NLV/Kashiwa 47/1997/JP strain.
Figure 9:
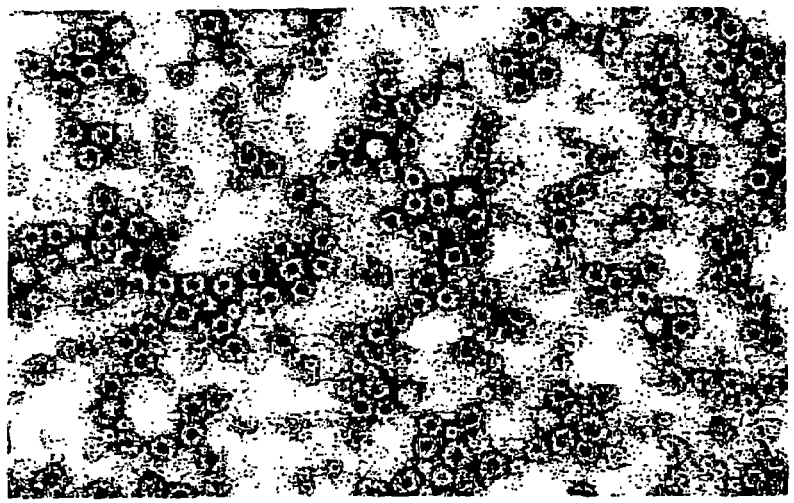
FIG. 9 is an electron micrograph (×100,00) of virus-like particles derived from the Hu/NLV/Mie 7 k/1994/JP strain.
Figure 10:
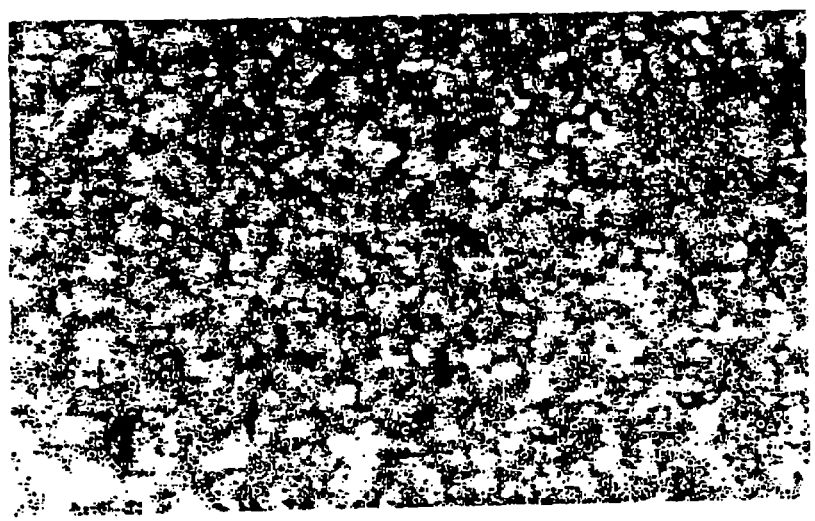
FIG. 10 is an electron micrograph (×100,00) of virus-like particles derived from the Hu/NLV/Kashiwa 645/1999/JP strain.
Figure 11:
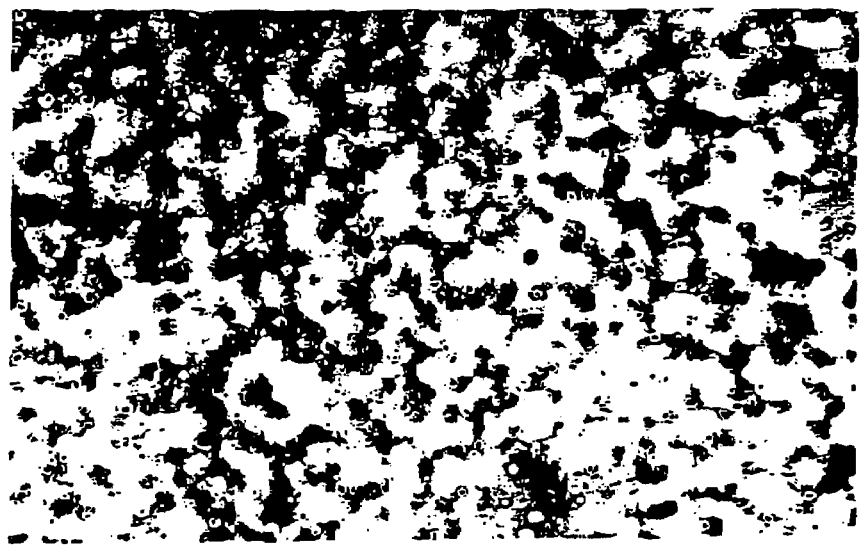
FIG. 11 is an electron micrograph (×100,00) of virus-like particles derived from the Hu/NLV/Osaka 10-25/1999/JP strain.

The purified SRSV virus-like particles were subjected to negative staining with uranyl acetate, and were then examined by an electron microscope to ascertain whether or not virus-like particles had been formed (FIGS. 2 to 12).

Example 5

Preparation of Immune Antibodies and Labeled by Use of Antibodies Virus-like Particles (1) Preparation of Immune Antibodies Against Virus-like Particles A phosphate buffer (pH 7.2, 1 mL)—which contained the purified SRSV virus-like particles (500 ig) obtained from one of the Hu/NLV/Kashiwa 645/1999/JP strain, the Hu/NLV/Seto 124/1989/JP strain, the Hu/NLV/Funabashi 258/1996/JP strain, the Hu/NLV/Chiba 407/1987/JP strain, the Hu/NLV/Narita 104/1997/JP strain, Hu/NLV/Sanbu 809/1998/JP strain, the Hu/NLV/Ichikawa 754/1998/JP strain, the Hu/NLV/Chitta 1876/1996/JP strain, the Hu/NLV/Kashiwa 47/1997/JP strain, the Hu/NLV/Mie 7 k/1994/JP strain, and the Hu/NLV/Osaka 10-25/1999/JP strain—and the Freund's incomplete adjuvant (1 mL) were mixed, and then immunized to a New Zealand white rabbit (3 kg) in a manner known per se in the art. Three weeks later, the rabbit was immunized further with a mixture of a phosphate buffer (pH 7.2, 1 mL), which contained the SRSV virus-like particles (0.25 ig), and the Freund's incomplete adjuvant (1 mL) (booster dose). Additional 3 weeks later, immunization was conducted as in the booster dose, and about 7 to 10 days after the additional booster dose, exsanguination was conducted, and the serum component was separated.

After the separated and purified serum was subjected to ammonium sulfate fractionation, the relevant fraction was dialyzed overnight at 4° C. against 50 mM Tris-HCl (pH 7.6). The inner dialyzate was then subjected to DEAE Sepharose chromatography which had been equilibrated with 50 mM Tris-HCl (pH 7.6). Under monitoring at an UV wavelength of 280 nm, an O.D. peak was collected to obtain an DEAE-purified IgG antibody (anti-SRSV antibody) against the virus-like particles.

(2) Preparation of Labeled Antibodies

Each anti-SRSV antibody was labeled with POD by an improved periodic acid technique ["Koso Men-eki Sokuteiho (Enzyme Immunoassay)", 2, 91, 1982]. Described specifically, POD was dissolved at 4 mg/mL in distilled water and 0.1 M sodium periodate (0.2 mL) was added, followed by a reaction at room temperature for about 20 minutes. The reaction mixture was then dialyzed overnight against 1 mM sodium acetate buffer (pH 4.0). Subsequent to the dialysis, 0.2 M sodium carbonate buffer (pH 9.5, 0.02 mL) was added to adjust the pH to 9.5, and at the same time, the anti-SRSV antibody (8 mg) was added.

After having been allowed to react at room temperature for 2 hours, 4 mg/mL sodium borohydroxide (0.1 mL) was added, followed by a reaction at 4° C. for about 2 hours. After the reaction, gel filtration was conducted with "Sephacryl S-200" while using 10 mM phosphate buffer. Under monitoring at an UV wavelength of 280 nm, a POD-labeled anti-SRSV antibody fraction was collected.

(3) Preparation of a Solid-phase Anti-SRSV Antibody Microplate

The anti-SRSV antibodies were separately diluted with a carbonate buffer (pH 9.5) to a concentration of from 0.5 to 10 ig/mL and then poured at 100 iL/well into a polystyrene flat-bottom microplate (manufactured by Nunc). The microplate was then allowed to stand overnight 4° C. After standing for 18 hours or longer, the microplate was washed 3 to 4 times at 200 iL/well with PBS which contained "Tween 20" at a final concentration of 0.05%. 10 mM PBS (pH 7.2)—which contained bovine serum albumin (BSA) and "Tween 20" at final concentrations of 0.5% and 0.05%, respectively—was then added at 200 iL/well. The microplate was allowed to stand overnight 4° C. to obtain a solid-phase anti-SRSV antibody microplate.

Example 6

Cross-reactivity (1) Antigen Detection ELISA

The purified SRSV virus-like particles of each group were diluted to 4 ng/mL to 0.04 ng/mL with a solution containing bovine serum albumin (BSA) and "Tween 20" at final concentrations of 0.2% and 0.05%, respectively, in a buffer (10 mM PBS, pH 7.2).

Then, the diluted emulsions of the virus-like particles (VLPs) were each added at 100 iL/well to wells of the corresponding solid-phase anti-SRSV antibody microplate, followed by a reaction at room temperature for 60 minutes. After the reaction, the reaction mixtures in the wells were eliminated under suction. 10 mM PBS (pH 7.2) which contained "Tween 20" at a final concentration of 0.05% was added at 200 iL/well to the wells, and was then eliminated under suction likewise. This procedure was repeated at least three times. After washing, the POD-labeled anti-SRSV antibody of the corresponding serotype, which had been diluted 20000-fold with a buffer, was added at 100 iL/well, followed by a reaction at room temperature for 60 minutes. Subsequent to washing, a TMB solution with hydrogen peroxide contained therein was added at 100 iL/well, followed by a reaction at room temperature for 30 minutes. After the reaction, 0.6 N sulfuric acid was added at 100 iL/well, and the absorbance (450 nm/630 nm) of each well was measured by an ELISA autoreader. The results are shown in Table 2.

TABLE 2

| | | Cross-reactivity between Serotypes | | | | | | | | | | |
|---|---|---|---|---|---|---|---|---|---|---|---|---|
| | VLP concen- | Solid-phase antibody plate × POD (top: strain name, bottom: dilution of POD-labeled antibody) | | | | | | | | | | |
| Purified VLP | tration (ng/mL) | 124 20000 | 258 20000 | 407 20000 | 645 20000 | 104 20000 | 809 20000 | 754 20000 | 1876 20000 | 47 20000 | 7k 20000 | 10-25 20000 |
| 124 | 4 | 1.430 | 0.018 | 0.013 | 0.016 | 0.013 | 0.007 | 0.007 | 0.008 | 0.010 | 0.019 | 0.009 |
| | 0.4 | 0.192 | 0.011 | 0.010 | 0.011 | 0.014 | 0.007 | 0.007 | 0.008 | 0.011 | 0.018 | 0.009 |
| | 0.04 | 0.030 | 0.011 | 0.011 | 0.011 | 0.013 | 0.007 | 0.007 | 0.009 | 0.012 | 0.018 | 0.009 |
| 258 | 4 | 0.042 | 1.831 | 0.114 | 0.020 | 0.015 | 0.009 | 0.007 | 0.010 | 0.012 | 0.019 | 0.010 |
| | 0.4 | 0.013 | 0.270 | 0.022 | 0.013 | 0.016 | 0.009 | 0.007 | 0.009 | 0.013 | 0.019 | 0.011 |
| | 0.04 | 0.008 | 0.043 | 0.012 | 0.011 | 0.017 | 0.008 | 0.007 | 0.009 | 0.012 | 0.018 | 0.010 |

TABLE 2-continued

Cross-reactivity between Serotypes

| Purified VLP | VLP concen-tration (ng/mL) | 124 20000 | 258 20000 | 407 20000 | 645 20000 | 104 20000 | 809 20000 | 754 20000 | 1876 20000 | 47 20000 | 7k 20000 | 10-25 20000 |
|---|---|---|---|---|---|---|---|---|---|---|---|---|
| 407 | 4 | 0.084 | 0.045 | 0.974 | 0.010 | 0.015 | 0.007 | 0.007 | 0.009 | 0.011 | 0.018 | 0.009 |
|  | 0.4 | 0.016 | 0.012 | 0.134 | 0.010 | 0.013 | 0.007 | 0.008 | 0.009 | 0.011 | 0.018 | 0.009 |
|  | 0.04 | 0.009 | 0.010 | 0.025 | 0.011 | 0.014 | 0.007 | 0.007 | 0.008 | 0.011 | 0.019 | 0.009 |
| 645 | 4 | 0.149 | 0.034 | 0.023 | 0.320 | 0.016 | 0.008 | 0.008 | 0.009 | 0.011 | 0.020 | 0.010 |
|  | 0.4 | 0.024 | 0.013 | 0.012 | 0.045 | 0.017 | 0.009 | 0.008 | 0.009 | 0.012 | 0.019 | 0.011 |
|  | 0.04 | 0.010 | 0.010 | 0.011 | 0.014 | 0.015 | 0.009 | 0.008 | 0.008 | 0.012 | 0.021 | 0.011 |
| 104 | 4 | 0.007 | 0.009 | 0.009 | 0.010 | 0.708 | 0.007 | 0.015 | 0.025 | 0.017 | 0.031 | 0.009 |
|  | 0.4 | 0.010 | 0.009 | 0.009 | 0.010 | 0.094 | 0.008 | 0.008 | 0.011 | 0.013 | 0.020 | 0.009 |
|  | 0.04 | 0.009 | 0.009 | 0.010 | 0.011 | 0.024 | 0.008 | 0.007 | 0.009 | 0.012 | 0.020 | 0.009 |
| 809 | 4 | 0.013 | 0.012 | 0.012 | 0.011 | 0.114 | 0.877 | 0.047 | 0.143 | 0.046 | 0.080 | 0.017 |
|  | 0.4 | 0.010 | 0.010 | 0.011 | 0.011 | 0.030 | 0.134 | 0.013 | 0.033 | 0.018 | 0.028 | 0.013 |
|  | 0.04 | 0.009 | 0.010 | 0.010 | 0.010 | 0.017 | 0.022 | 0.008 | 0.011 | 0.014 | 0.020 | 0.011 |
| 754 | 4 | 0.008 | 0.011 | 0.009 | 0.010 | 0.038 | 0.008 | 0.286 | 0.068 | 0.025 | 0.027 | 0.013 |
|  | 0.4 | 0.008 | 0.009 | 0.010 | 0.011 | 0.017 | 0.008 | 0.038 | 0.015 | 0.013 | 0.020 | 0.010 |
|  | 0.04 | 0.009 | 0.009 | 0.011 | 0.011 | 0.016 | 0.008 | 0.011 | 0.010 | 0.012 | 0.020 | 0.009 |
| 1876 | 4 | 0.010 | 0.012 | 0.011 | 0.011 | 0.026 | 0.009 | 0.013 | 0.728 | 0.023 | 0.025 | 0.012 |
|  | 0.4 | 0.009 | 0.014 | 0.010 | 0.011 | 0.017 | 0.009 | 0.008 | 0.089 | 0.015 | 0.021 | 0.013 |
|  | 0.04 | 0.011 | 0.010 | 0.010 | 0.012 | 0.016 | 0.010 | 0.007 | 0.017 | 0.014 | 0.019 | 0.011 |
| 47 | 4 | 0.008 | 0.009 | 0.009 | 0.010 | 0.017 | 0.007 | 0.008 | 0.011 | 0.324 | 0.021 | 0.014 |
|  | 0.4 | 0.008 | 0.009 | 0.009 | 0.011 | 0.015 | 0.008 | 0.008 | 0.009 | 0.048 | 0.020 | 0.013 |
|  | 0.04 | 0.008 | 0.009 | 0.009 | 0.011 | 0.014 | 0.008 | 0.008 | 0.008 | 0.017 | 0.022 | 0.011 |
| 7k | 4 | 0.009 | 0.010 | 0.010 | 0.011 | 0.019 | 0.009 | 0.010 | 0.011 | 0.015 | 0.160 | 0.014 |
|  | 0.4 | 0.009 | 0.011 | 0.010 | 0.011 | 0.016 | 0.008 | 0.008 | 0.008 | 0.015 | 0.035 | 0.016 |
|  | 0.04 | 0.011 | 0.010 | 0.010 | 0.011 | 0.017 | 0.009 | 0.008 | 0.009 | 0.014 | 0.022 | 0.015 |
| 10-25 | 4 | 0.009 | 0.010 | 0.010 | 0.011 | 0.098 | 0.010 | 0.022 | 0.069 | 0.033 | 0.058 | 1.050 |
|  | 0.4 | 0.007 | 0.009 | 0.010 | 0.011 | 0.026 | 0.009 | 0.009 | 0.020 | 0.018 | 0.026 | 0.163 |
|  | 0.04 | 0.009 | 0.009 | 0.009 | 0.012 | 0.016 | 0.009 | 0.007 | 0.011 | 0.015 | 0.023 | 0.029 |
| Blank |  | 0.009 | 0.011 | 0.010 | 0.011 | 0.016 | 0.009 | 0.008 | 0.009 | 0.017 | 0.022 | 0.016 |

In the table, "645" indicates the Hu/NLV/Kashiwa 645/1999/JP strain, "124" the Hu/NLV/Seto 124/1989/JP strain, "258" the Hu/NLV/Funabashi 258/1996/JP strain, "407" the Hu/NLV/Chiba 407/1987/JP strain, "104" the Hu/NLV/Narita 104/1997/JP strain, "809" the Hu/NLV/Sanbu 809/1998/JP strain, "754" the Hu/NLV/Ichikawa 754/1998/JP strain, "1876" the Hu/NLV/Chitta 1876/1996/JP strain, "47" the Hu/NLV/Kashiwa 47/1997/JP strain, "7 k" the Hu/NLV/Mie 7 k/1994/JP strain, and "10-25" the Hu/NLV/Osaka 10-25/1999/JP strain.

As a result, no cross-reactivity was observed between viruses of the same genogroup, to say nothing of cross-reactivity between viruses of different Genogroups I and II. It was, therefore, confirmed that the serotypes of the 11 types of used virus strains were different from one another.

Test 1 Discrimination of SRSVs in Genogroup

The anti-SRSV antibodies against the SRSVs belonging to Genogroup I (the Hu/NLV/Kashiwa 645/1999/JP strain, the Hu/NLV/Seto 124/1989/JP strain, the Hu/NLV/Funabashi 258/1996/JP strain, and the Hu/NLV/Chiba 407/1987/JP strain) were diluted with a carbonate buffer (pH 9.5) to a concentration of from 0.5 to 10 ig/mL and were then mixed. The thus-obtained mixture was poured at 100 iL/well into a polystyrene flat-bottom microplate (manufactured by Nunc). The microplate was allowed to stand overnight at 4° C. After standing for 18 hours or longer, the microplate was washed 3 to 4 times at. 200 iL/well with PBS which contained "Tween 20" at a final concentration of 0.05%. 10 mM PBS (pH 7.2)—which contained bovine serum albumin (BSA) and "Tween 20" at final concentrations of 0.5% and 0.05%, respectively—was then added at 200 iL/well. The microplate was allowed to stand overnight at 4° C. to obtain a microplate with the anti-SRSV-IgG antibodies against the respective serotypes of Genogroup I carried in a mixed solid-phase form (Type I plate).

Next, the anti-SRSV antibodies against the SRSVs belonging to Genogroup II (the Hu/NLV/Narita 104/1997/JP strain, the Hu/NLV/Sanbu 809/1998/JP strain, the Hu/NLV/Ichikawa 754/1998/JP strain, the Hu/NLV/Chitta 1876/1996/JP strain, the Hu/NLV/Kashiwa 47/1997/JP strain, the Hu/NLV/Mie 7 k/1994/JP strain, and the Hu/NLV/Osaka 10-25/1999/JP strain) were similarly formed into a solid phase to obtain a Type II plate.

To feces (0.5 to 1.0 g) of each SRSV patient, PBS (9 mL) and "Daiflon" (1 mL) were added, followed by homogenization. The thus-prepared suspension was centrifuged under 19,000 g for 20 minutes, and the supernatant was collected and formed into a 10% fecal emulsion. The 10% fecal emulsion was diluted at 1:1 in volume with a buffer. The diluted emulsion was added at 100 iL/well into wells of the Type I and Type II plates, and was allowed to react at room temperature for 60 minutes. After the reaction, the reaction mixtures in the wells were eliminated under suction. 10 mM PBS (pH 7.2)—which contained "Tween 20" at a final concentration of 0.05%—was added at 200 iL/well to the wells, and was then eliminated under suction. This procedure was performed at least three times. After the washing, the POD-labeled anti-SRSV antibodies of the respective serotypes, said antibodies having had been diluted 20,000-fold with a buffer, were added at 100 iL/well, and were then reacted at room temperature for 60 minutes. After washing, a TMB solution with hydrogen peroxide contained therein was added at 100 iL/well, and were then reacted at room temperature for 30 minutes. Subsequent to the reaction, 0.6 N sulfuric acid was added at 100 iL/well, and the absorbance (450 nm/630 nm) of each well was measured by an ELISA autoreader.

As a result, it was found that among 15 fecal specimens from patients infected to SRSV of Genogroup I, 14 fecal specimens reacted only to the Type I plate and did not react to the Type II plate. Concerning 7 fecal specimens from patients infected to SRSV of Genogroup II, on the other hand, 6 fecal specimens did not react to the Type I plate but reacted only to Type II plate. It has, therefore, been confirmed that discrimination in genogroup is actually feasible.

Test 2 Discrimination of SRSVs in Serotype

The anti-SRSV antibodies against the SRSVs (the Hu/NLV/Kashiwa 645/1999/JP strain, the Hu/NLV/Seto 124/1989/JP strain, the Hu/NLV/Funabashi 258/1996/JP strain, the Hu/NLV/Chiba 407/1987/JP strain, the Hu/NLV/Narita 104/1997/JP strain, the Hu/NLV/Sanbu 809/1998/JP strain, the Hu/NLV/Ichikawa 754/1998/JP strain, the Hu/NLV/Chitta 1876/1996/JP strain, the Hu/NLV/Kashiwa 47/1997/JP strain, the Hu/NLV/Mie 7 k/1994/JP strain, and the Hu/NLV/Osaka 10-25/1999/JP strain) were each independently diluted with a carbonate buffer (pH 9.5) to a concentration of from 0.5 to 10 ig/mL. The thus-obtained dilutions were poured at 100 iL/well into a polystyrene flat-bottom microplate (manufactured by Nunc) The microplate was allowed to stand overnight at 4° C. After having been allowed to stand for 18 hours or longer, the microplate was washed 3 to 4 times at 200 iL/well with PBS which contained "Tween 20" at a final concentration of 0.05%. 10 mM PBS (pH 7.2)—which contained bovine serum albumin (BSA) and "Tween 20" at final concentrations of 0.5% and 0.05%, respectively—was then added at 200 iL/well. The microplate was allowed to stand overnight at 4° C. to obtain a solid-phase anti-SRSV antibody microplate (serotype discrimination plate).

With respect to fecal specimens from SRSV patients, ELISA was conducted in a similar manner as in Test 1. The results are shown in Table 3.

TABLE 3

Clinical Test
Total number of specimens: 41

| Serotype discriminated by invention kit | Number of detected specimen(s) |
| --- | --- |
| HU/NLV/Kashiwa 645/1999/JP | 1 |
| Hu/NLV/Seto 124/1989/JP | 7 |
| Hu/NLV/Funabashi 258/1996/JP | 4 |
| Hu/NLV/Chiba 407/1987/JP | 1 |
| HU/NLV/Narita 104/1997/JP | 4 |
| Hu/NLV/Sanbu 809/1998/JP | 12 |
| Hu/NLV/Ichikawa 754/1998/JP | 2 |
| Hu/NLV/Chitta 1876/1996/JP | 3 |
| Hu/NLV/Kashiwa 47/1997/JP | 1 |
| Hu/NLV/Mie 7k/1994/JP | 1 |
| Hu/NLV/Osaka 10-25/1999/JP | 2 |
| Total number of detected specimens | 38 (93%) |

As a result, it has been found that according to the SRSV detection method of the present invention, SRSVs can be detected with a probability as high as 93% and their serotypes can also be discriminated.

Further, the serotypes discriminated by the kit of the present invention were consistent with those ascertained by PCR and an analysis of their base sequences (Table 4).

TABLE 4

Ascertainment of Serotypes
Total number of specimens: 38

| Serotype discriminated by invention kit | | Number of specimen(s) discriminated in serotype by PCR and analysis of base sequences |
| --- | --- | --- |
| HU/NLV/Kashiwa 645/1999/JP | 1 Specimens | 1 |
| Hu/NLV/Seto 124/1989/JP | 7 Specimens | 7 |
| Hu/NLV/Funabashi 258/1996/JP | 4 Specimens | 4 |
| Hu/NLV/Chiba 407/1987/JP | 1 Specimen | 1 |
| HU/NLV/Narita 104/1997/JP | 4 Specimens | 4 |
| Hu/NLV/Sanbu 809/1998/JP | 12 Specimens | 12 |
| Hu/NLV/Ichikawa 754/1998/JP | 2 Specimens | 2 |
| Hu/NLV/Chitta 1876/1996/JP | 3 Specimens | 3 |
| Hu/NLV/Kashiwa 47/1997/JP | 1 Specimen | 1 |
| Hu/NLV/Mie 7k/1994/JP | 1 Specimen | 1 |
| Hu/NLV/Osaka 10-25/1999/JP | 2 Specimens | 2 |

The anti-SRSV antibodies against the SRSVs (the Hu/NLV/Kashiwa 645/1999/JP strain, the Hu/NLV/Seto 124/1989/JP strain, the Hu/NLV/Funabashi 258/1996/JP strain, the Hu/NLV/Chiba 407/1987/JP strain, the Hu/NLV/Narita 104/1997/JP strain, the Hu/NLV/Sanbu 809/1998/JP strain, the Hu/NLV/Ichikawa 754/1998/JP strain, the Hu/NLV/Chitta 1876/1996/JP strain, the Hu/NLV/Kashiwa 47/1997/JP strain, the Hu/NLV/Mie 7 k/1994/JP strain, and the Hu/NLV/Osaka 10-25/1999/JP strain) were each independently diluted with a carbonate buffer (pH 9.5) to a concentration of from 0.5 to 10 ig/mL. All the dilutions so obtained were mixed. As an alternative, the anti-SRSV antibodies may be diluted after mixing them together. Using the thus-diluted mixture of the anti-SRSV antibodies, a solid-phase anti-SRSV antibody microplate was produced likewise. With respect to 22 fecal specimens from patients infected to SRSV, ELISA was conducted in a similar manner as in Test 1. It was possible to detect SRSV in 20 specimens.

INDUSTRIAL APPLICABILITY

According to the SRSV detection kit of the present invention, it is possible to detect most of the SRSV-related viruses discovered to date and also to discriminate their serotypes and genogroups. When SRSV-related food poisoning occurs, the SRSV detection kit of the present invention is, therefore, useful for specifying an infection route, preventing the infection from spreading, and performing an epidemiological investigation.

The invention claimed is:

1. An isolated HU/NLV/Kashiwa 47/1997/JP polynucleotide having a base sequence represented by SEQ ID NO: 20 or a base sequence having at least 80% homology to SEQ ID NO:20.

2. A vector, comprising the isolated HU/NLV/Kashiwa 47/1997/JP polynucleotide of claim 1.

3. The HU/NLV/Kashiwa 47/1997/JP polynucleotide of claim 1 having the base sequence represented by SEQ ID NO: 20.

4. A vector, comprising the isolated HU/NLV/Kashiwa 47/1997/JP polynucleotide of claim 3.

5. The HU/NLV/Kashiwa 47/1997/JP polynucleotide of claim 1 having at least 80% homology to SEQ ID NO:20.

6. A vector, comprising the isolated HU/NLV/Kashiwa 47/1997/JP polynucleotide of claim 5.

7. A method of preparing an SRSV virus-like particle, comprising introducing the vector of claim 2 into insect cells under conditions suitable for expression of a protein encoded by the isolated polynucleotide, wherein the vector is a recombinant baculovirus; and collecting virus-like particles from the insect cells.

8. A method of preparing an SRSV virus-like particle, comprising introducing the vector of claim 4 into insect cells under conditions suitable for expression of a protein encoded by the isolated polynucleotide, wherein the vector is a recombinant baculovirus; and collecting virus-like particles from the insect cells.

9. A method of preparing an SRSV virus-like particle, comprising introducing the vector of claim 6 into insect cells under conditions suitable for expression of a protein encoded by the isolated polynucleotide, wherein the vector is a recombinant baculovirus; and collecting virus-like particles from the insect cells.

* * * * *